(12) United States Patent
Curry et al.

(10) Patent No.: US 7,305,112 B2
(45) Date of Patent: Dec. 4, 2007

(54) METHOD OF CONVERTING RARE CELL SCANNER IMAGE COORDINATES TO MICROSCOPE COORDINATES USING RETICLE MARKS ON A SAMPLE MEDIA

(75) Inventors: Douglas N. Curry, Menlo Park, CA (US); Richard H. Bruce, Los Altos, CA (US); Robert T. Krivacic, San Jose, CA (US); Huangpin B. Hsieh, Mountain View, CA (US); Richard A. Lerner, La Jolla, CA (US)

(73) Assignees: The Scripps Research Institute, LaJolla, CA (US); Palo Alto Research Center Incorporated, Palo Alto, CA (US)

( * ) Notice: Subject to any disclaimer, the term of this patent is extended or adjusted under 35 U.S.C. 154(b) by 740 days.

(21) Appl. No.: 10/740,972

(22) Filed: Dec. 19, 2003

(65) Prior Publication Data
US 2004/0131241 A1    Jul. 8, 2004

Related U.S. Application Data

(63) Continuation-in-part of application No. 10/616,366, filed on Jul. 9, 2003, now Pat. No. 7,277,569, which is a continuation-in-part of application No. 10/271,347, filed on Oct. 15, 2002, now Pat. No. 7,113,624.

(51) Int. Cl.
*G06K 9/00* (2006.01)

(52) U.S. Cl. .................................. 382/133; 382/128

(58) Field of Classification Search ................ 382/128, 382/129, 130, 131, 132, 133, 134; 356/73, 356/237.2, 244, 394, 431, 445, 495; 436/46, 436/63, 74, 519; 250/461.2, 255; 128/902, 128/905
See application file for complete search history.

(56) References Cited

U.S. PATENT DOCUMENTS 4,002,829 A    1/1977    Hutchison
(Continued)

FOREIGN PATENT DOCUMENTS

GB    1 579 188    11/1980
(Continued)

OTHER PUBLICATIONS

European Search Report, dated Apr. 5, 2006; EPC Application No. 05112479.0-2204; Berlin.
(Continued)

*Primary Examiner*—Samir Ahmed
*Assistant Examiner*—Abolfazl Tabatabai
(74) *Attorney, Agent, or Firm*—Fay Sharpe LLP

(57) ABSTRACT

Provided is a method for obtaining a position of an object. A slide which carries at least one object and has reticle marks arranged at positions which form substantially a right angle, is positioned in a slide holder of a first imaging system. A first coordinate space of the imaging system is defined, and coordinates of the reticle marks in the first coordinate space are designated. A second coordinate space of a second imaging system is defined, and the coordinates of the reticle marks in the second coordinate space is designated. Using the designated coordinates of the reticle marks of the first coordinate space, the coordinate conversion parameters are computed. Thereafter, coordinates of at least one object in the first coordinate space are designated, and the first coordinate space coordinates of the object are converted into unique coordinates in a second coordinate space, using the coordinate conversion parameters.

23 Claims, 17 Drawing Sheets

U.S. PATENT DOCUMENTS

| | | | |
|---|---|---|---|
| 4,010,364 | A | 3/1977 | Fuwa |
| 4,556,903 | A | 12/1985 | Blitchington et al. |
| 4,600,951 | A | 7/1986 | Blitchington |
| 4,721,851 | A | 1/1988 | Kogure |
| 4,849,645 | A | 7/1989 | Mendenko et al. |
| 4,875,780 | A | 10/1989 | Moran et al. |
| 4,941,309 | A | 7/1990 | Fluent et al. |
| 5,017,798 | A | 5/1991 | Murakami et al. |
| 5,216,485 | A | 6/1993 | Bird et al. |
| 5,220,617 | A | 6/1993 | Bird et al. |
| 5,315,993 | A | 5/1994 | Alcala |
| 5,471,066 | A * | 11/1995 | Hagiwara ............... 250/559.48 |
| 5,627,365 | A | 5/1997 | Chiba et al. |
| 5,640,246 | A | 6/1997 | Castonguay |
| 5,651,047 | A | 7/1997 | Moorman et al. |
| 5,732,162 | A | 3/1998 | Curry |
| 5,798,831 | A | 8/1998 | Hagiwara |
| 5,801,390 | A * | 9/1998 | Shiraishi ................... 250/559.3 |
| 5,835,262 | A * | 11/1998 | Iketaki et al. ................ 359/352 |
| 5,892,577 | A | 4/1999 | Gordon |
| 6,278,957 | B1 * | 8/2001 | Yasuda et al. ............... 702/150 |
| 6,411,386 | B1 * | 6/2002 | Nishi .......................... 356/401 |
| 6,445,451 | B1 | 9/2002 | Douglas-Hamilton et al. |
| 6,545,334 | B2 | 4/2003 | Verhaegen |
| 6,582,363 | B2 | 6/2003 | Adachi et al. |
| 6,636,623 | B2 | 10/2003 | Nelson et al. |
| 2001/0046712 | A1 | 11/2001 | Hang et al. |
| 2002/0177885 | A1 | 11/2002 | Eisfeld et al. |

FOREIGN PATENT DOCUMENTS

| | | |
|---|---|---|
| JP | 4296642 | 10/1992 |
| JP | 6148085 | 5/1994 |
| JP | 9145631 A | 6/1997 |

OTHER PUBLICATIONS

European Search Report, dated Jun. 2, 2006; EPC Application No. 05112370.1-2204.

Bianchi, Diana W., et al., Fetomaternal Cellular and Plasma DNA Trafficking, The Yin and the Yang, *Annals New York Academy of Sciences*, pp. 119-131.

Wolfe, Josh, A Thousand Dots of Light, *Forbes/Wolfe Nanotech Report*, May 29, 2002, www.Forbes.com.

Pertl, Barbara, MD, et al., Fetal DNA in Maternal Plasma: Emerging Clinical Applications, *The American College of Obstetricians and Gynecologists*, Published by Elsevier Science Inc., vol. 98, No. 3, Sep. 2001, pp. 483-490.

EP 03 25 6441, European Search Report, Jan. 20, 2004.

Bauer, Kenneth D., et al., Reliable and Sensitive Analysis of Occult Bone Marrow Metastases Using Automated Cellular Imaging, *Clinical Cancer Research*, vol. 6, pp. 3552-3559, Sep. 2000.

Witzig, Thomas E., et al., Detection of Circulating Cytokeratin-positive Cells in the Blood of Breast Cancer Patients Using Immunomagnetic Enrichment and Digital Microscopy, *Clinical Cancer Research*, vol. 8, 1085-1091, May 2002.

Ghossein, R.A., et al., Molecular Detection and Characterisation of Circulating Tumour Cells and Micrometastases in Solid Tumours, *European Journal of Cancer* 36 (2000) 1681-1694, Mar. 2000, Elsevier Science Ltd.

Flatmark, Kjersti, et al., Immunomagnetic Detection of Micrometastatic Cells in Bone Marrow of Colorectal Cancer Patients, *Clinical Cancer Research*, vol. 8, 444-449, Feb. 2002.

Mehes, Gábor, et al., Quantitative Analysis of Disseminated Tumor Cells in the Bone Marrow by Automated Fluorescence Image Analysis, *Cytometry (Communications in Clinical Cytometry)*, 42:357-362 (2000, Wiley-Liss, Inc.

Werther, M., et al., The Use of the CELLection Kit in the Isolation of Carcinoma Cells from Mononuclear Cell Suspensions, *Journal of Immunological Methods*, 238 (2000) 133-141, 2000 Elsevier Science B.V.

Burchill, SA, et al., Comparison of the RNA-Amplification Based Methods RT-PCR and NASBA for the Detection of Circulating Tumour Cells, *2002 Cancer Research Campaign, British Journal of Cancer* (2002) 86, 102-109.

* cited by examiner

FAST Scanner Coordinate Conversion Spreadsheet | Rev. 3 | 07/21/2003 | FSXYCOORD.COM
slide #:

Step 1: Fill in IMAGE orig., x-ret., y-ret., slide number. Compute "Coordinates".
Step 2: Fill in MICROSCOPE orig., x-ret., y-ret. Compute "Coordinates".

| IMAGE | x | y |
|---|---|---|
| origin | 850 | 150 |
| yreticle | 840 | 1400 |
| xreticle | 460 | 160 |
| slide.mm | 38 | 18.5 |

|  | x | y |
|---|---|---|
|  | -10 | 1250 |
|  | -390 | 10 |
| ang. | -3.11596 | -178.351 |

| MSCOPE | x | y |
|---|---|---|
| origin | -705 | 1090 |
| yret. | -700 | 2930 |
| xret. | 3070 | 1080 |

|  | x | y | r |
|---|---|---|---|
|  | 5 | 1840 | 1840.007 |
|  | 3775 | -10 | 3775.013 |
| dltaYret |  |  |  |
| dltaXret |  |  |  |

$r_y$ = 42.03747, -1249.33
$r_x$ = 390.1282, 1.21E-13
nrmlz. 0.097404, 0.014808
dsqu. -0.03365

| | rad | deg | scale |
|---|---|---|---|
| alpha | -0.00265 | -0.15178 | horiz. 99.34245 |
| beta | 3.138875 | 179.8443 | vert. -99.4598 |
| gama | -3.14152 | -179.996 | tanGama 6.84E-05 |

248 IMAGE Hit Data | 250 Shifted Scanner Coordinates | Rotated Scanner Coordinates | 252 Independent Coordinates | 254 Skewed & Scaled Scope Coordinates | 256 Rotated Microscope Coordinates | 258 Converted Microscope Coordinates

| # | x | y | x | y | x | y | x | y | x | y | x | y | x | y |
|---|---|---|---|---|---|---|---|---|---|---|---|---|---|---|
|  | 850 | 150 | 0 | 0 | 0 | 0 | 0 | 0 | 0 | 0 | 0 | 0 | -705 | 1090 |
|  | 840 | 1400 | -10 | 1250 | 42.03747 | -1249.33 | -18.5 | 38 | 0.12583 | 1840.07 | 5 | 1840 | -700 | 2930 |
|  | 460 | 160 | -390 | 10 | 390.1282 | 1.21E-13 | 38 | 1.8E-15 | 3775.01 | -1.8E-13 | 3775 | -10 | 3070 | 1080 |
| 1 | 1000 | 2132 | 150 | 1982 | -99.147 | -1985.19 | -16.1636 | -29.3966 | -1605.54 | 2923.78 | -1597.79 | 2928.02 | -2302.79 | 4018.02 |
| 2 | 1340 | 4353 | 490 | 4203 | -382.11 | -4214.18 | -51.03 | -62.4031 | -5069.1 | 6206.61 | -5052.59 | 6220.01 | -5757.59 | 7310.01 |
| 3 | 4500 | 222 | 3650 | 72 | -3646.96 | -165.54 | -355.77 | -2.4512 | -35343.1 | 243.80 | -35342.3 | 337.422 | -36047.3 | 1437.42 |
| 4 | 644 | 5321 | -206 | 5171 | 338.479 | -5164.02 | 16.0444 | -76.4683 | -1594.41 | 7605.53 | -1614.55 | 7601.28 | 909.547 | 8691.28 |
| 5 | 2094 | 932 | 1244 | 782 | -1223.55 | -813.63 | -121.845 | -12.0482 | -12104.3 | 1198.31 | -12101.1 | 1230.37 | -12806.1 | 2320.38 |
| 6 | 5964 | 1333 | 5114 | 1183 | -5082 | -1313.7 | -499.312 | -19.4531 | -49602.7 | 1934.8 | -49597.4 | 2066.19 | -50302.4 | 3156.19 |
| 7 | 0 | 0 | -850 | -150 | 845.876 | 171.738 | 82.9545 | 2.54309 | 8240.88 | -252.93 | 8240.18 | -274.76 | 7535.18 | 815.236 |
| 8 | 0 | 0 | -850 | -150 | 845.876 | 171.738 | 82.9545 | 2.54309 | 8240.88 | -252.93 | 8240.18 | -274.76 | 7535.18 | 815.236 |
| 9 | 0 | 0 | -850 | -150 | 845.876 | 171.738 | 82.9545 | 2.54309 | 8240.88 | -252.93 | 8240.18 | -274.76 | 7535.18 | 815.236 |
| 10 | 0 | 0 | -850 | -150 | 845.876 | 171.738 | 82.9545 | 2.54309 | 8240.88 | -252.93 | 8240.18 | -274.76 | 7535.18 | 815.236 |
| 11 | 0 | 0 | -850 | -150 | 845.876 | 171.738 | 82.9545 | 2.54309 | 8240.88 | -252.93 | 8240.18 | -274.76 | 7535.18 | 815.236 |
| 12 | 0 | 0 | -850 | -150 | 845.876 | 171.738 | 82.9545 | 2.54309 | 8240.88 | -252.93 | 8240.18 | -274.76 | 7535.18 | 815.236 |

FIG. 12

230 — Reverse Direction

232':

| MSCOPE | x | y |
|---|---|---|
| origin | -7050 | 10900 |
| yreticle | -7000 | 29300 |
| xreticle | 30700 | 10800 |
| slide.mm | 38 | 18.5 |

238':

| IMAGE | x | y |
|---|---|---|
| origin | 850 | 150 |
| yret. | 840 | 1400 |
| xret. | 4600 | 160 |

234:
| | x | y |
|---|---|---|
| yshift | 50 | 18400 |
| xshift | 37750 | -100 |
| ang. | 0.002649 | 0.151777 |

236:
| | x | y |
|---|---|---|
| ry | 1.258274 | 18400.07 |
| rx | 37750.13 | 0 |
| nrmlz. | 0.001007 | -0.00101 |
| dsqu. | 6.84E-05 | |

240:
| | x | y | r |
|---|---|---|---|
| dltaYret | -10 | 1250 | 1250.04 |
| dltaXret | 3750 | 10 | 3750.013 |

242:
| | rad | deg |
|---|---|---|
| alpha | 0.002667 | 0.152788 |
| beta | 3.149592 | 180.4584 |
| gama | -3.14693 | -180.306 |

244:
| | scale | |
|---|---|---|
| horiz. | 98.68456 | |
| vert. | -67.5688 | |
| tanGama | -0.00533 | |

246' Microscope Hit Data / 248' Shifted Microscope Coordinates / 250' Rotated Microscope Coordinates / 252' Independent Coordinates / 254' Skewed & Scaled Image Coordinates / 256' Rotated Image Coordinates / 258' Converted Image Coordinates

| # | Hit x | Hit y | Shift x | Shift y | Rot x | Rot y | Ind x | Ind y | Skew x | Skew y | RotImg x | RotImg y | Conv x | Conv y |
|---|---|---|---|---|---|---|---|---|---|---|---|---|---|---|
|  | -7050 | 10900 | 0 | 0 | 0 | 0 | 0 | 0 | 0 | 0 | 0 | 0 | 850 | 150 |
|  | -7000 | 29300 | 50 | 18400 | 1.25827 | 18400.07 | -18.5 | 0 | -6.66664 | 1250.02 | -10 | 1250 | 840 | 1400 |
|  | 30700 | 10800 | 37750 | -100 | 37750.1 | 0 | 0 | 38 | 3750.01 | 0 | 3750 | 10 | 4600 | 160 |
| 1 | -15625 | 8748.1 | -8574.5 | -2151.89 | -8568.74 | -2174.6 | -8.62531 | 2.18641 | -850.397 | -147.733 | -850 | -150 | 0 | 0 |
| 2 | -15625 | 8748.1 | -8574.5 | -2151.89 | -8568.74 | -2174.6 | -8.62531 | 2.18641 | -850.397 | -147.733 | -850 | -150 | 0 | 0 |
| 3 | -15625 | 8748.1 | -8574.5 | -2151.89 | -8568.74 | -2174.6 | -8.62531 | 2.18641 | -850.397 | -147.733 | -850 | -150 | 0 | 0 |
| 4 | -15625 | 8748.1 | -8574.5 | -2151.89 | -8568.74 | -2174.6 | -8.62531 | 2.18641 | -850.397 | -147.733 | -850 | -150 | 0 | 0 |
| 5 | -15625 | 8748.1 | -8574.5 | -2151.89 | -8568.74 | -2174.6 | -8.62531 | 2.18641 | -850.397 | -147.733 | -850 | -150 | 0 | 0 |
| 6 | -15625 | 8748.1 | -8574.5 | -2151.89 | -8568.74 | -2174.6 | -8.62531 | 2.18641 | -850.397 | -147.733 | -850 | -150 | 0 | 0 |
| 7 | -15625 | 8748.1 | -8574.5 | -2151.89 | -8568.74 | -2174.6 | -8.62531 | 2.18641 | -850.397 | -147.733 | -850 | -150 | 0 | 0 |
| 8 | -15625 | 8748.1 | -8574.5 | -2151.89 | -8568.74 | -2174.6 | -8.62531 | 2.18641 | -850.397 | -147.733 | -850 | -150 | 0 | 0 |
| 9 | -15625 | 8748.1 | -8574.5 | -2151.89 | -8568.74 | -2174.6 | -8.62531 | 2.18641 | -850.397 | -147.733 | -850 | -150 | 0 | 0 |
| 10 | -15625 | 8748.1 | -8574.5 | -2151.89 | -8568.74 | -2174.6 | -8.62531 | 2.18641 | -850.397 | -147.733 | -850 | -150 | 0 | 0 |
| 11 | -15625 | 8748.1 | -8574.5 | -2151.89 | -8568.74 | -2174.6 | -8.62531 | 2.18641 | -850.397 | -147.733 | -850 | -150 | 0 | 0 |
| 12 | -15625 | 8748.1 | -8574.5 | -2151.89 | -8568.74 | -2174.6 | -8.62531 | 2.18641 | -850.397 | -147.733 | -850 | -150 | 0 | 0 |

METHOD OF CONVERTING RARE CELL SCANNER IMAGE COORDINATES TO MICROSCOPE COORDINATES USING RETICLE MARKS ON A SAMPLE MEDIA

CROSS REFERENCE

This is a continuation-in-part of U.S. Ser. No. 10/616,366, Filed Jul. 9, 2003, now U.S. Pat. No. 7,277,569 which is a continuation-in-part of U.S. Ser. No. 10/271,347, filed Oct. 15, 2002, now U.S. Pat. No. 7,113,624 both documents hereby incorporated by reference in their entirety.

BACKGROUND

The present exemplary embodiments relate to the imaging arts, and find particular application in conjunction with low and high-density cell detection, locating, and identifying in blood smears, biological assays, and the like across distinct imaging systems, and will be described with particular reference thereto. However, it is to be appreciated the exemplary embodiments will also find application in imaging, locating and identifying other types of low- or high-density features on various substantially planar surfaces and samples, such as imaging semiconductor wafers, imaging particulate contaminants in fluids or thin solid films, and so forth, with such imaging finding specific uses in the printing arts, electronic arts, medical arts, and other scientific and engineering areas.

In rare cell studies, a particular problem arises due to the typically low concentration of the rare cells in the blood or other body fluid. In a typical rare cell study, blood is processed to remove cells that that are not needed. Then a fluorescent material is applied that attaches to antibodies, which in turn selectively attach to a cell surface or cellular protein of the rare cells. The cellular proteins may be membrane proteins or proteins within a cell, such as cytoplasm proteins. The antibodies may also attach to other types of molecules of the rare cell, as well as to DNA.

The fluorescent material may be a fluorescent marker dye or any other suitable material which will identify the cells of interest. A smear treated in this manner, which may include the blood and/or components of the blood, is prepared and optically analyzed to identify rare cells of the targeted type. For statistical accuracy it is important to obtain as large a number of cells as required for a particular process, in some studies at least ten rare cells should be identified, requiring a sampling of at least ten million cells, for a one-in-one-million rare cell concentration. Such a blood smear typically occupies an area of about 100 $cm^2$. It is to be understood, however, that this is simply one example and other numbers of cells may be required for statistical accuracy for a particular test or study. Other cell identifiers which are being used and investigated are quantum dots and nano-particle probes. Also, while a rare cell is mentioned as a one-in-one-million cell concentration, this is not intended to be limiting and is only given as an example of the rarity of the cells being sought. The concepts discussed herein are to be understood to be useful in higher or lower levels of cell concentration.

In this regard, the ability to scan large numbers of cells at a high rate is considered a key aspect which increases the throughput of testing processes. Therefore, it is considered valuable to provide a system which improves the speed, reliability and processing costs which may be achieved by cell detection systems and/or processes.

One particular cell detection technique is known as fluorescence in situ hybridization (FISH). This process uses fluorescent molecules to paint genes or chromosomes. The technique is particularly useful for gene mapping and for identifying chromosomal abnormalities. In the FISH process, short sequences of single-stranded DNA, called probes, are prepared and which are complementary to the DNA sequences which are to be painted and examined. These probes hybridize, or bind, to a complementary DNA, and as they are labeled with a fluorescent tag, it permits a researcher to identify the location of sequences of the DNA. The FISH technique may be performed on non-dividing cells.

Another process of cell detection is flow cytometry (FC), which is a means of measuring certain physical and chemical characteristics of cells or particles as they travel in suspension past a sensing point. Ideally the cells travel past the sensing point one by one. However, significant obstacles exist to achieving this ideal performance, and in practice a statistically relevant number of cells are not detected due to the cells bunching or clumping together, making it not possible to identify each cell individually. In operation a light source emits light to collection optics, and electronics with a computer translates signals to data. Many flow cytometers have the ability to sort, or physically separate particles of interest, from a sample.

Another cytometry process is known as laser scanning cytometry (LSC). In this system, data is collected by rastering a laser beam within the limited field of view (FOV) of a microscope. With laser rastering, the excitation is intense and for single or multiple wavelengths, filtering permits a differentiation between dyes responsive at distinct wavelengths. This method provides equivalent data of a flow cytometer, but is a slide based system. It permits light scatter and fluorescence, but also records the position of each measurement. By this design, cells of interest can be relocated, visualized, restained, remeasured and photographed.

While the above-noted systems are directed to creating faster scan rates, they nevertheless still have relatively small fields of view (FOV), such as microscopes. This will, therefore, still result in speeds which do not reach the desired scan rates.

In view of this, the previously noted and incorporated U.S. application Ser. Nos. 10/271,347 and 10/616,366 disclosed a fiber array scanning technology (FAST) that increases the speed at which scanning of a sample and the detection of potential or candidate rare cells may be accomplished, lending itself to the investigation of large samples.

These applications addressed the issue that while use of the described FAST scan system provides significant benefits in the detection of potential or candidate rare cells, the resolution obtainable by the FAST system may not be sufficient for certain studies. U.S. Ser. No. 10/616,366 addressed this issue by describing a system where a sample—is provided following scanning in the FAST scan system—to a device having a higher resolution than may be obtained by the described FAST scan system permitting an increased level of investigation. A particular type of high resolution device is a fluorescent microscope, or any other imaging system such as previously described herein or otherwise known. The high resolution device is described as either being integrated with the FAST scan system, or once the FAST scan process has been completed, the sample (or a data file containing an image of the sample) is transferred to a separate high-resolution device for more specific identification of rare cells.

A particular concern with undertaking this additional investigation, is acquiring location information of the designated candidate rare cells when the sample is transferred from the FAST scan system to the high resolution system. Since, as mentioned the number of cells being scanned in an investigation may be from one million to 50 million or more, where the rare cells may be at a very low concentration. Therefore, when these candidate rare cells—identified in the FAST scan system—are transferred to a microscope system, locating these one-in-a-million cells, even when previously identified, is a time-consuming and at times nearly impossible task.

In order to improve the investigation process, it is important to be able to designate the locations of the detected candidate rare cells in the FAST scan system and to determine corresponding location information for use in a high resolution investigation.

Presently, this is accomplished by a user attempting to visually identify an area on a sample where the candidate rare cells have been detected. However, this is a time-consuming, inaccurate process, and does not lend itself to high-speed review and investigations.

Issues related to the transfer of candidate rare cells from the FAST scan system to a higher resolution system is that the higher resolution system has a small field of view (FOV), and that the two systems have distinct positional coordinate spaces. Therefore, even when locations of the candidate rare cells are identified in the FAST scan system coordinate space, this information is not usable when the candidate rare cells are transferred to the higher resolution system. Likewise, when coordinate locations are observed in the higher resolution system, it is sometimes desirable to backward locate those positions into the original FAST scan coordinate system.

BRIEF DESCRIPTION OF THE INVENTION

Provided is a method for obtaining a position of an object. A slide which carries at least one object and has reticle marks arranged at positions which form substantially a right angle, is positioned in a slide holder of a first imaging system. A first coordinate space of the imaging system is defined, and coordinates of the reticle marks in the first coordinate space are designated. A second coordinate space of a second imaging system is defined, and the coordinates of the reticle marks in the second coordinate space is designated. Using the designated coordinates of the reticle marks of the first coordinate space, the coordinate conversion parameters are computed. Thereafter, coordinates of at least one object in the first coordinate space are designated, and the first coordinate space coordinates of the object are converted into unique coordinates in a second coordinate space, using the coordinate conversion parameters.

BRIEF DESCRIPTION OF THE DRAWINGS

The invention may take form in various components and arrangements of components, and in various steps and arrangements of steps. The drawings are only for purposes of illustrating preferred embodiments and are not to be construed as limiting the invention.

FIGS. 11A-11D are used to describe operation of a FAST scanner coordinate conversion process as generally identified in FIG. 6; and FIG. 12 provides a FAST scanner coordinate conversion output for a reverse direction from FIG. 11.

DETAILED DESCRIPTION

Figure 1:
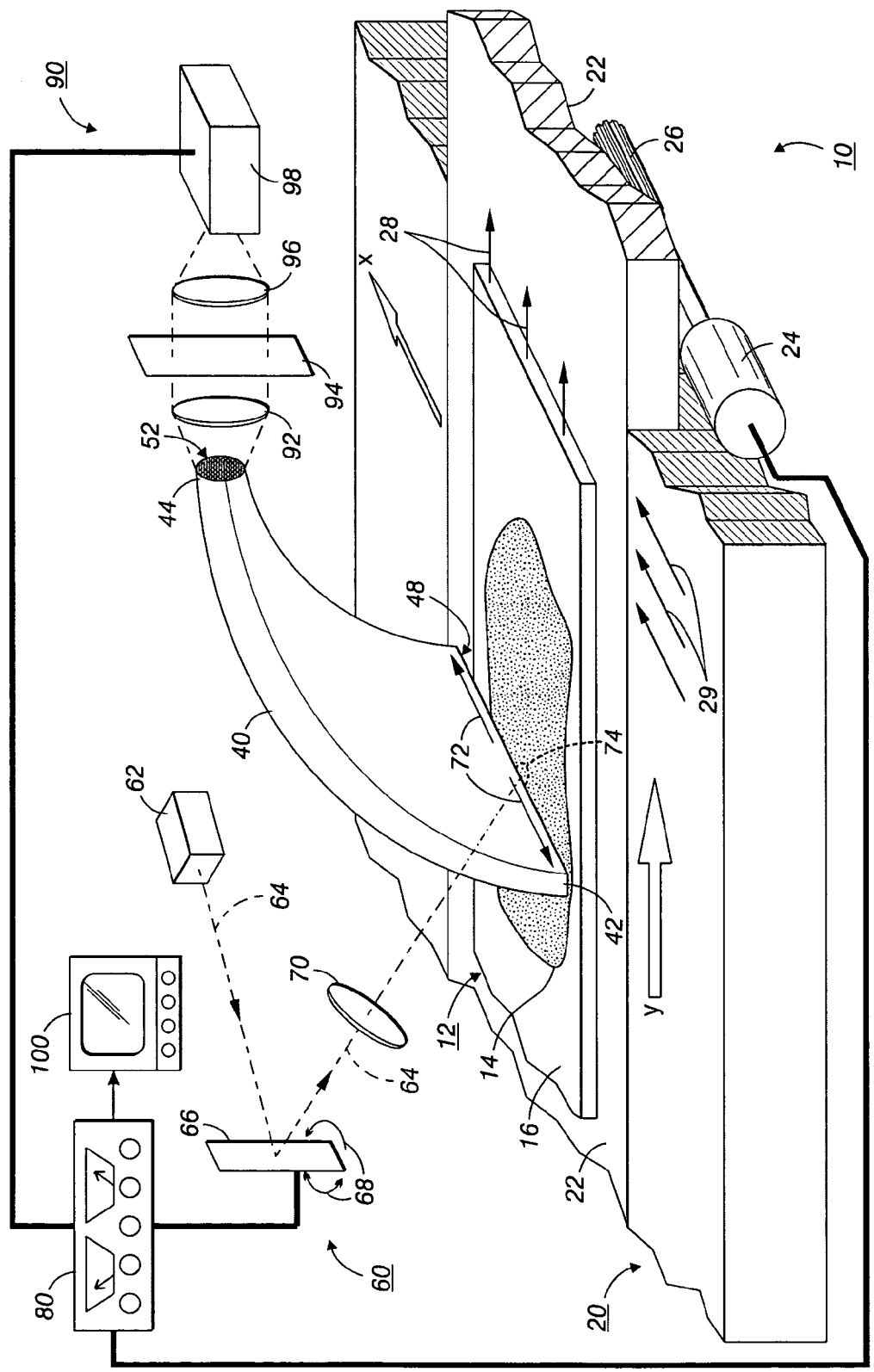
FIG. 1 shows a perspective view of an imaging apparatus formed in accordance with a preferred embodiment of the invention.

With reference to FIG. 1, an imaging apparatus or imager 10 examines a sample 12 such as a biological smear 14 disposed on at least a portion of a surface of a slide 16. Imaging apparatus or imager 10, as expanded upon below, is designed for detection of minute or microscopic material.

As is known in the art, for cell studies the sample 12 is suitably prepared by drawing a sample of a biological fluid such as, but not limited to, blood or parts of blood from a subject. In a preferred embodiment, the sample is a monolayer of cells. The fluid sample is treated with a fluorescent material, such as but not limited to a marker dye, that selectively bonds to different kinds of biological molecules, which may be on the surface or inside the cell, such as proteins, nucleic acids or other molecules. Suitable markers are known in the art for marking a number of different cell types of clinical interest, including selected cancer cell types, fetal cells, or other appropriate cells to be considered. Work is also being undertaken to develop marking materials for numerous other cells such as brain cells, liver cells, as well as bacteria cells, among others. The material preferably emits a characteristic output, such as a fluorescence or a phosphorescence, responsive to a selected excitation irradiation, such as irradiation by a selected wavelength or spectrum of light, x-ray irradiation, electron-beam irradiation, or the like. The characteristic luminescence typically has a characteristic wavelength or spectral range of wavelengths. While dyes are the predominant tagging process, other techniques exist including the use of markers known as quantum dots and DNA nano-particle probes.

The sample 12 is mounted on an imager translation stage, or slide holder, 20 (shown in part) which includes a linearly translatable track 22 that supports the sample 12. A motor 24 connects with the track 22 via gearing 26 to translate the track 22 and the supported sample 12 along a y-direction (indicated by arrows 28) and a x-direction (indicated by arrows 29). Although translation stage 20 driven by a rotary motor 24 is shown in FIG. 1, it is also contemplated to employ other types of mechanical driving devices. Furthermore, other types of sample movement such as sample rotation are also contemplated.

Figure 2:
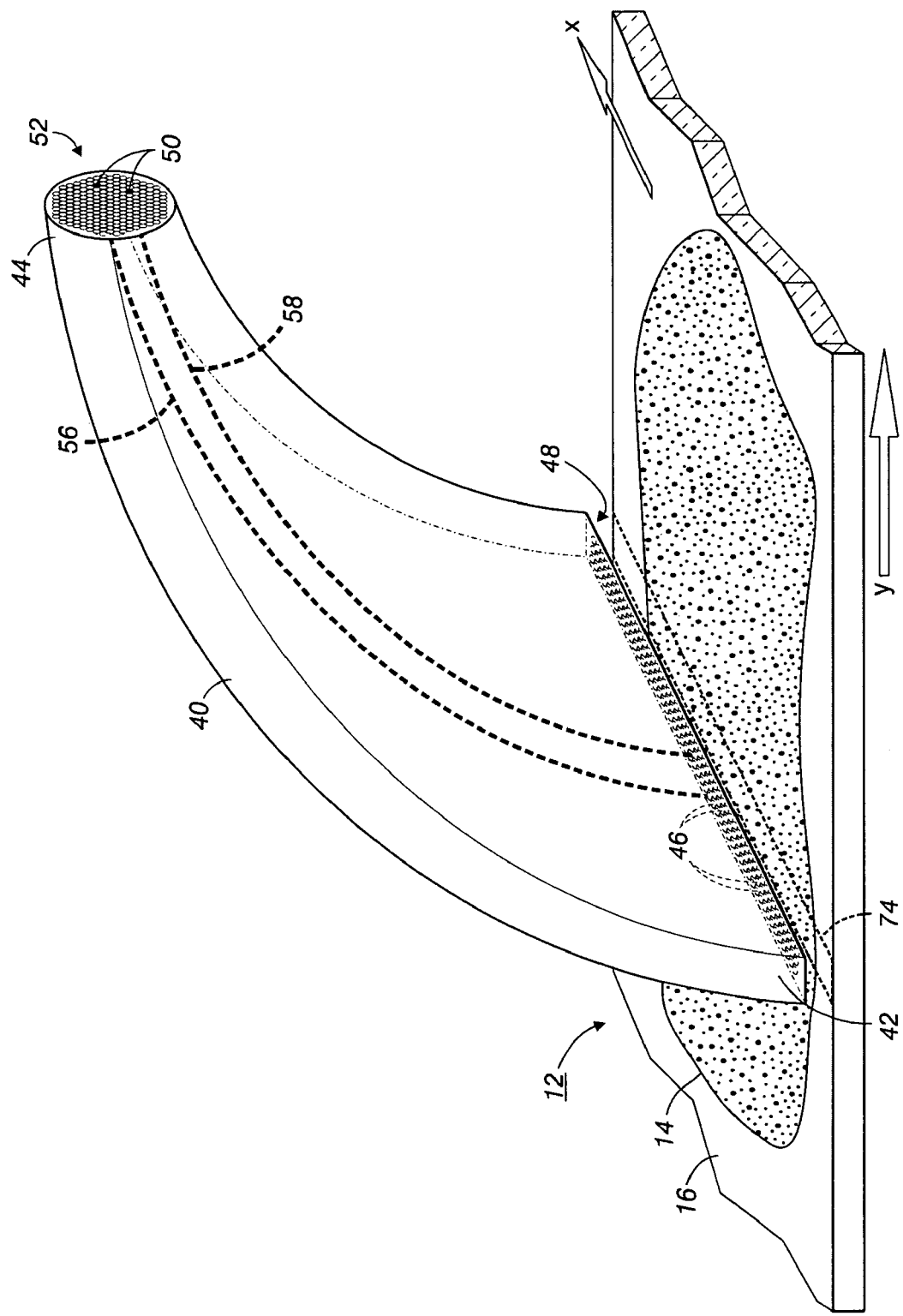
FIG. 2 shows an enlarged perspective view of the morphed fiber optic bundle of the imaging apparatus of FIG. 1 in relation to the sample.
Figure 3:
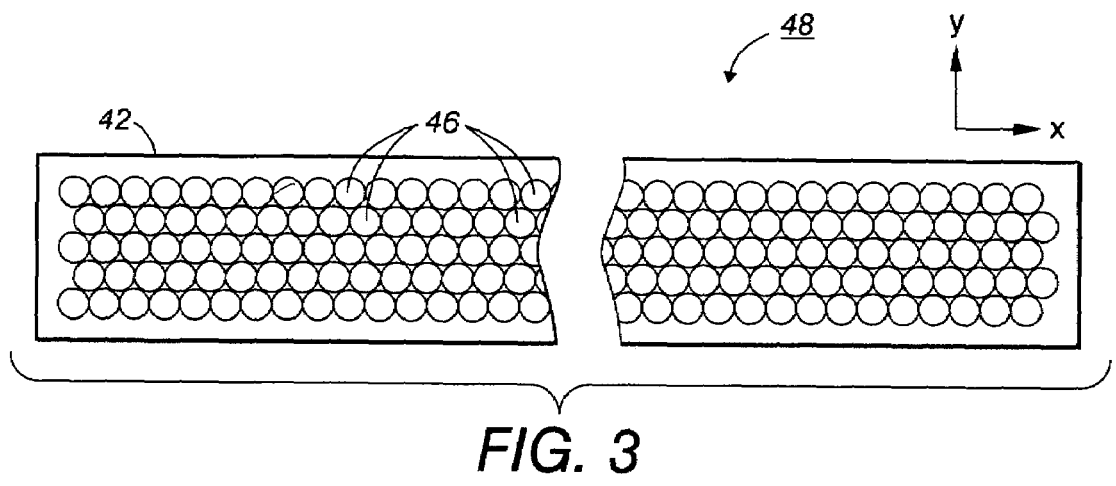
FIG. 3 shows an enlarged end view of the first end that defines the input aperture of the morphed fiber optic bundle of the apparatus of FIG. 1.

With continuing reference to FIG. 1 and with further reference to FIGS. 2 and 3, a fiber optic bundle 40 includes a first end 42 that is proximate to the sample 12, and a second end 44 that is distal from the sample 12. The first end 42 includes a plurality of first fiber ends 46 arranged substantially parallel to one another in an arrangement that defines a generally linear or high-aspect-ratio rectangular input aperture 48 (best seen schematically in FIG. 3) with a long dimension aligned with the x-direction. The input aperture 48 preferably includes a large number of first fiber ends 46, i.e. thousands of fiber ends. In one suitable embodiment, 40,000 fibers each having an approximately 50 micron diameter are arranged into a 40 fiber-by-1000 fiber array to define the input aperture 48 with a long dimension of approximately 5 cm and a short dimension of about 0.2 cm corresponding to a 25:1 aspect ratio. The first fiber ends 46 can be arranged in a regular pattern, as shown in FIG. 3. Alternatively, the first fiber ends can be arranged in an irregular or non-periodic array and may have diameters which are greater or less than 50 microns. Although generally round fiber ends are shown, it is also contemplated to employ fibers with oval, square, hexagonal, or other cross-sectional shapes. The first fiber ends 46 are oriented substantially perpendicular to the plane of the biological smear 14 so as to view the smear 14.

The optical fiber bundle 40 "morphs" or changes cross-sectional dimensions and shape between the first end 42 to the second end 44 such that the second end 44 includes a plurality of second fiber ends 50 (best seen schematically in FIG. 2) that define a compact, generally circular output aperture 52. Preferably, there is a one-to-one correspondence between the first fiber ends 46 and the second fiber ends 50, and each first fiber end connects with a second fiber end by an individual, distinct fiber having its own waveguiding cladding. Alternatively, each fiber can include only a light-transmissive fiber core, and an ambient/core interface functions to waveguide the light. Other optical fiber types can also be used, such fibers being well known in the art and typically formed of glass, plastic, or other light-transmissive materials by extrusion methods. In FIG. 2, the paths of two exemplary individual, distinct fibers 56, 58 are indicated as dotted lines. The morphed shape of the fiber bundle 40 from an extended, generally linear first end 42 to a compact, generally circular second end 44 is preferably formed by varying a spatial arrangement of the fibers of the optical fiber bundle 40 in a continuous fashion. For the exemplary 40,000 fiber embodiment with each fiber having a 50 micron diameter, the generally circular output aperture 52 has a circular diameter of about 1.3 cm.

It is particularly pointed out that the spatial relationship between the first fiber ends 46 and the second fiber ends 50 is generally arbitrary. For example, in FIG. 2 the fibers 56, 58 run from approximately the same position in the input aperture 48. However, the fiber 56 terminates near a top of the output aperture 52, while the fiber 58 terminates near a middle of the output aperture 52. Although for convenience in arranging the fibers it is contemplated to arrange the first and second fiber ends 46, 50 in the respective apertures 48, 52 with a selected correspondence relative to one another, the fiber ends 46, 50 can instead have a generally uncorrelated and arbitrary relationship therebetween. Morphed fiber optic bundles similar to the fiber optic bundle 40 are known and used in the optical arts for other applications such as transforming focused light into a linear illumination pattern, and for coupling a light beam into a linear slit of a monochromator or spectrometer.

To obtain good light transmission, the fiber optic bundle 40 preferably has a high fiber packing factor, for example, fiber optic bundle 40 has a packing factor of about 0.80 or higher. Other factors influencing the light transmission include the polishing or light transmission properties of the tips of the first and second fiber ends 46, 50, the absorption per unit length of the fibers 56, 58, and the overall length of the fibers 56, 58. Fiber bending losses are preferably reduced by avoiding sharp bends of the fiber optic bundle 40. For example, as seen in FIGS. 1 and 2, the difference in orientation of the input aperture 48 and the output aperture 52 is achieved by a gradual bend in the optical fiber bundle 40.

With continuing reference to FIGS. 1-3, a scanning radiation (light) source 60 in a suitable embodiment includes a laser 62 that produces excitation light (radiation beam) 64 at a wavelength or wavelength range selected to excite the material used in marking the biological smear 14. The excitation light 64 is angularly scanned by a galvanometer 66 that has a reflective surface that rotates (indicated by curved arrows 68) responsive to an electrical input. An optional focusing lens 70 focuses the angularly scanned excitation light 64 onto the sample 12, and more particularly onto the biological smear 14. The angular scanning produced by the galvanometer 66 translates into a linear sweeping or fast scanning (indicated by arrows 72) of the excitation light on the biological smear 14 along a linear trajectory 74 arranged below the input aperture 48 and parallel to the long dimension of the input aperture 48. That is, using the coordinate system of FIG. 1 the linear trajectory 74 is parallel to the x-direction. In a suitable embodiment, the trajectory 74 is disposed on the biological smear 14 about one millimeter below the input aperture 48, although other distances will be appropriate dependant upon devices and the environment in which these concepts are implemented.

For cell studies, the excitation radiation 64 preferably produces a spot size on the biological smear 14 which substantially comports with a size of the cells, which may vary in size but are typically about one to thirty microns in size. To obtain such narrow beam focusing, the focusing lens 70 is typically included.

With continuing reference to FIGS. 1-3, an electronic control unit 80 communicates with the galvanometer 66 and the translation stage 20 to coordinate the linear sweeping or scanning 72 of the radiation beam 64 along the trajectory 74 and the linear translation 28 of the sample 12 to effectuate a rastering of the radiation beam 64 across a selected area of the sample which is bounded in the x-direction by the smaller of a span of the trajectory 74 and the long dimension of the input aperture 42. Preferably, the span of the trajectory 74 substantially comports with the long dimension of the input aperture 42.

Excitation radiation beam 64 is incident upon the biological smear 14 at an oblique angle which is larger than a collection angle θ of the input aperture 42. The collection angle θ depends upon a short dimension of the input aperture 42, the distance between the input aperture 42 and the biological smear 14, and the light collecting characteristics of the first fiber ends 46. The latter is suitably characterized by a numerical aperture of the fiber ends. As is known in the art, an optical fiber end typically has a large numerical aperture corresponding to a large light collection angle which is particularly advantageous for collecting the typically weak characteristic luminescence of the cells. In a suitable embodiment, the radiation beam 64 impinges upon the sample 12 at 30°-90°, and preferably about 60o off the normal.

Because the incidence angle of the radiation beam 64 is larger than the collection angle θ of the input aperture 42, specularly reflected radiation is not collected by the input aperture 42. However, the characteristic luminescence produced by the treated cells generally emits uniformly in all spatial directions, i.e. each treated cell corresponds to a point light source. Hence, a substantial portion of the characteristic luminescence is collected by the input aperture 42 due to its close proximity to and alignment with the radiation beam trajectory 74 on the biological smear 14 as well as the large numerical aperture of the first fiber ends 46. The collected light enters the first fiber ends 46, transmits along the individual fibers, e.g. the fibers 56, 58 shown in FIG. 2, and exits the optical fiber bundle 40 at second fiber ends 50 that correspond to the collecting first fiber ends 46.

It will be appreciated that the characteristic luminescence produced by a particular cell will not generally be collected by all or even most of the first fiber ends 46. Rather, only one or a few of the first fiber ends 46 which are closely proximate to the cell will collect the characteristic luminescence therefrom. In an exemplary embodiment, the radiation spot size is about 10-15 microns corresponding to a similarly sized cell, while each first fiber end 46 has a diameter of about 50 microns. Hence, only one or a few fibers may be needed to view and collect the characteristic luminescence for any given position of the sweeping radiation beam 64.

However, because at the second end 44 of the fiber bundle 40 the second fiber ends 50 are arranged to define the compact, output aperture 52, the characteristic luminescence emanates from a small region of space corresponding to the output aperture 52 regardless of which of the first fiber ends 46 collected the characteristic luminescence. As the excitation beam 64 sweeps along its trajectory 74 parallel to and typically below the input aperture 48, the proximate one or few of the first fiber ends 46 collect the characteristic luminescence, which is channeled by the fiber optic bundle 40 to the compact output aperture 52.

In one suitable embodiment, the blocking filter 94 is an interference filter with a reflectance peak coinciding with a center wavelength of the radiation beam 64 is employed. As is known in the art, optical interference filters have a rejection ratio that is strongly dependent upon the angle of incidence of the light. An exemplary interference filter used in one actually constructed embodiment exhibits a 106:1 or greater rejection ratio for light incident within ±14° of normal incidence. In this constructed embodiment, the first lens 92 includes a lens combination, designed using known optical design methods, that collimates light emanating from the output aperture 52 to within a ±10° angular divergence.

With continuing reference to FIG. 1, a second lens 96 focuses the collimated collected light onto a photodetector arrangement 98. By combining the compact output aperture 52 with focusing optics 92, 96, photodetector 98, which may be a single photodetector, provides signal detection for the spatially distributed linear input aperture 48. Because of the typically low collected characteristic luminescence intensities produced by treated cells, the photodetector 98 is preferably a photomultiplier tube. As is known in the art, a photomultiplier tube provides substantial signal gain through cascade multiplication of electrons in a multi-stage high-voltage cathode. To further improve the signal-to-noise ratio, the optical path of the signal detector 90 is preferably enclosed to substantially reduce noise due to stray light.

With continuing reference to FIG. 1, the electronic control unit 80 communicates with the galvanometer 66 and the translation microscope stage 20 to raster the radiation beam 64 across the sample. Characteristic luminescence produced by interaction of the radiation beam 64 with treated cells in the biological smear 14 is collected by the input aperture 48, channeled to the output aperture 52 by the optical fiber bundle 40, and detected by the signal detector 90. The electronic control unit 80 receives the detected signal from the photodetector 98, and correlates the detected signal with positional coordinates of the radiation beam 64 on the sample 12.

In particular, the electronic control unit 80 identifies a beam sweep position as a first coordinate in the x-direction, and a position of the translation stage 20 as a second orthogonal coordinate in the y-direction, to spatially map out the collected characteristic luminescence intensity as a function of position on the sample 12. The x- and y-coordinates can be inferred from the laser scan velocity and stage translation velocities, respectively. Alternately, registration marks on the sample media can be included to identify absolute x,y position information. In addition, one or both of the galvanometer 66 and the translation stage 20 can include a position sensor which is read by the electronic control unit 80 to ascertain the coordinates of the radiation beam 64 on the sample. The electronic control unit 80 suitably formats the detected signal and spatial coordinates information and stores the information in an internal memory, writes the information to a non-volatile storage medium such as a magnetic or optical disk, formats and displays an image representation including an array of picture elements with coordinates mapped to the spatial coordinates information and an intensity or color mapped to the detected signal intensity on a display 100, or the like.

When working with such small structures, noise—such as dirt or dust particles, or miscellaneous cells—may be found on the sample 12, and will have an effect on the acquired image information. Specifically, the imager 10 may accumulate image data irrelevant to the identification of rare cells. At times this noise may be considered as "false positives." It is desirable to eliminate this noise (including false positives) during image acquisition and processing. Therefore, filtering procedures may be implemented via electronic control unit 80 and/or other elements of the system 10 to eliminate information not related to rare cells. The filtering techniques may use various characteristics of an image event to perform the filtering operations, including the number of pixels, intensity, phase and shape of the image event under consideration.

In one embodiment, an image event may be classified as a non-rare cell or a rare cell image event by counting the number of pixels of the image event under investigation.

In another filtering embodiment, the shape of an image event is used to filter non-relevant information. Specifically, in many instances an image event correlating to a rare cell or cluster of rare cells would have a known shape corresponding to the rare cells being imaged, and blurred by the impulse response of the radiation spot. If the detected shape is other than expected for the pertinent rare cell and/or clusters of rare cells, this would indicate the detected image event is noise such as a dust or dirt particle or other irrelevant signal from the sample.

Still a further filtering process which may be used to identify rare cell image events from non-rare cell image events is by tracking the intensity of the image event under investigation. For example, in the discussion related to the phase of the 10 micron structure, it would be expected that a higher intensity would be detected for rare cell image events that were in phase with the pixel acquisition phase, and would also provide fewer pixels. Out of phase image events would have their energy shared with several neighboring pixels, thereby providing a smaller intensity per pixel, but more pixels. In addition, in some non-specific binding of tags on cells, i.e., cells not related to the rare cells, may produce image events but these would have a lower intensity than the expected intensity from rare cell binding clusters.

The foregoing thus describes a fiber array scanning technology (FAST) that increases the speed at which scanning of a sample and detection of rare cells may be accomplished, it therefore lends itself to the investigation of large samples. A benefit of scanning large samples is particularly relevant to the investigation of rare cells, where the potential of false negative results are of specific concern. A false negative result indicates a particular type of cell was not found, when in fact the cell does exist. This result may lead to potential misdiagnosing of a patient as healthy when, in fact, a medical problem exists.

Cell detection systems presently in use commonly place the biological smears on a slide having a dimension of 2.5 by 7.5 centimeters (or about 1 inch by 3 inches). Using the scan techniques of the present application, large areas may be scanned efficiently, and slides of 7.5 centimeters by 12.5 centimeters (or about 3 by 5 inches), 15 by 15 centimeters (or about 6 by 6 inches) or larger may be used. Again, one of the reasons for the speed of the described scanning process is use of the wide input aperture and fast scanning laser beam that nevertheless permits sufficiently high resolution to detect the rare cells.

Figure 4A:
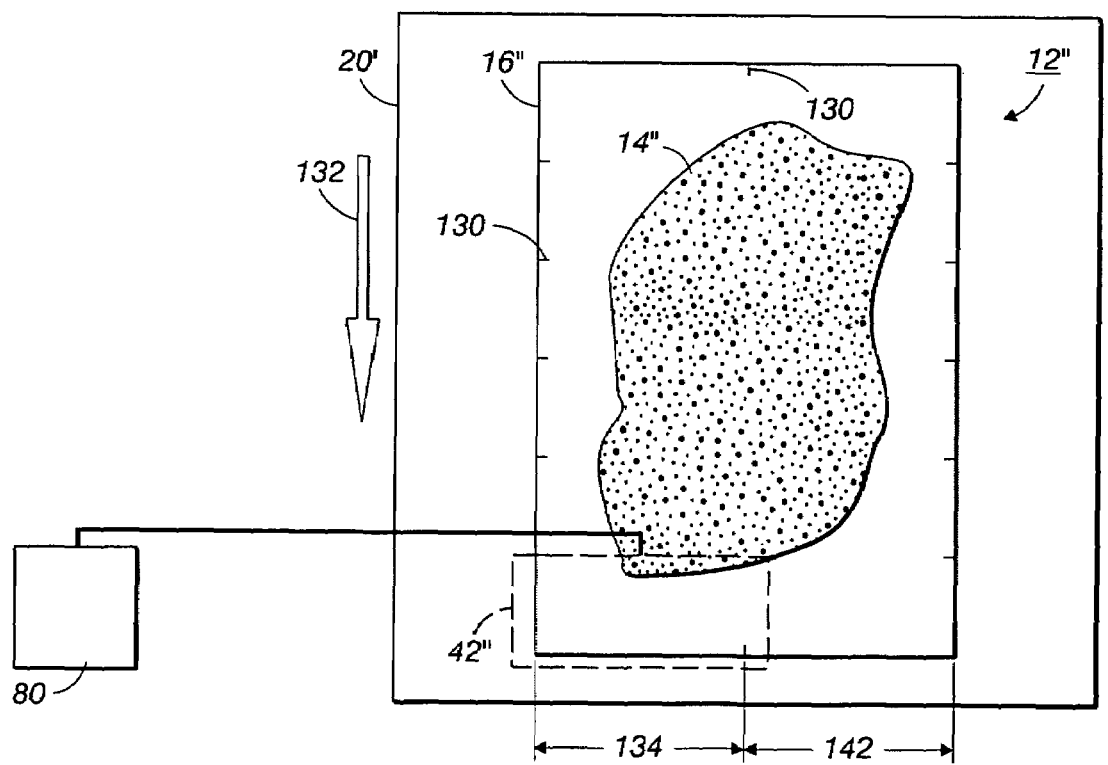
FIGS. 4A-4C illustrate an enlarged sample area and an embodiment for a higher resolution investigation.
Figure 4B:
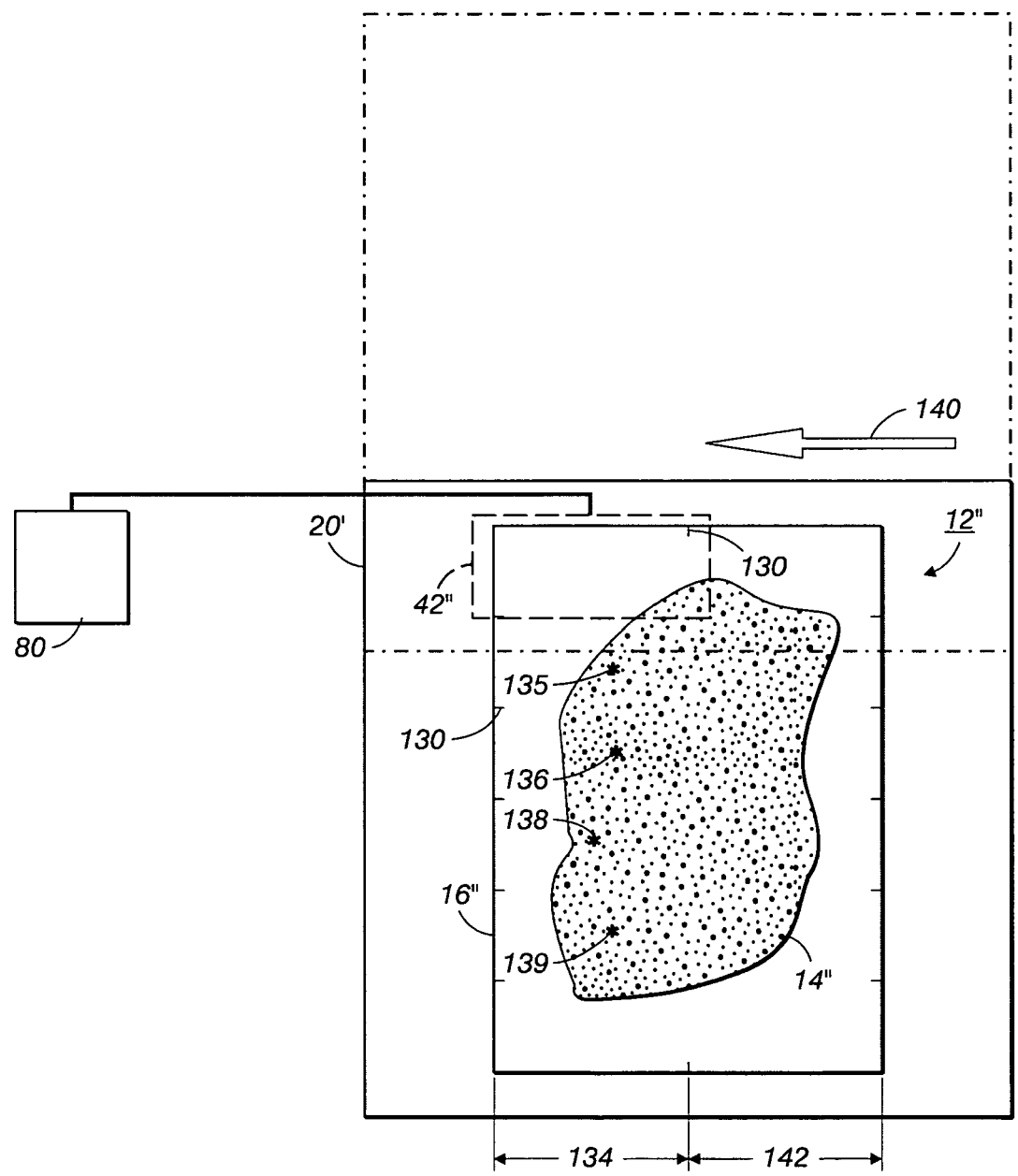
Figure 4C:
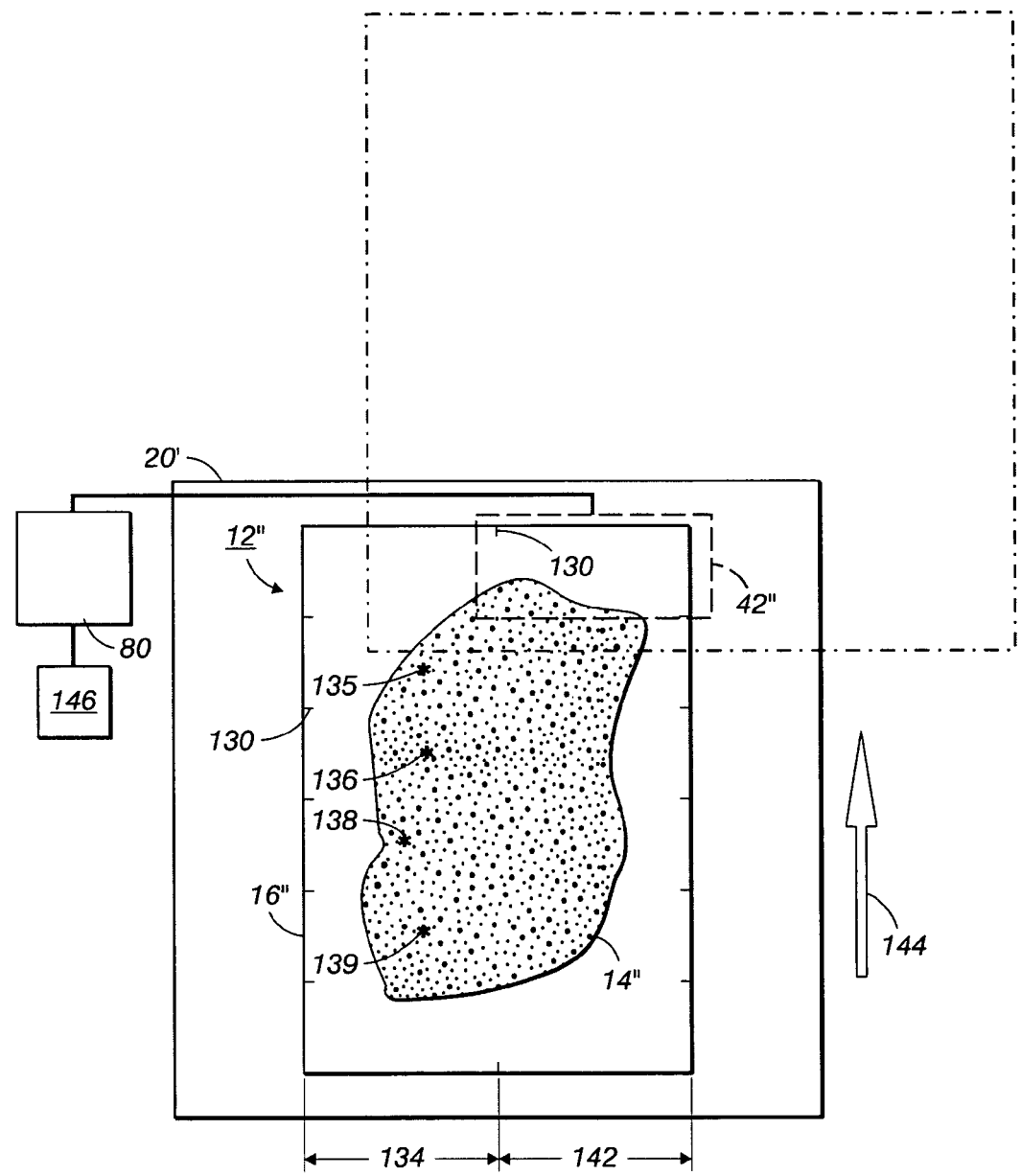

An implementation of scanning large samples is now described with attention to FIGS. 4A-4C, wherein FIG. 4A illustrates that a sample 12", such as a biological smear 14" disposed on at least a portion of a surface of a slide 16", is wider than first end 42" which forms an input aperture such as input aperture 48 of FIG. 1. The sample 12" is on translation stage 20' in a manner illustrated, for example, with the gearing and structural arrangement shown in FIG. 1.

Slide 16" incorporates registration marks 130 to assist in obtaining positional information of detected rare cells to be identified and saved. The position identification information may be obtained through use of registration (reticle) marks or through other position detection techniques. The reticle marks can be pre-printed on the surface of the slide or applied before, during, or after the sample is applied to the slide, or positioned on a frame that may be holding the slide.

In either case, the translation stage 20' is operated in accordance with the gearing shown in FIG. 1. As the translation stage is moved in the direction of arrow 132 (i.e., arrows 28 of FIG. 1), the input aperture of first end 42", in conjunction with the laser scanning operations previously described, acts to detect and identify fluorescing cells within a first portion 134 of sample 12". The translation stage continues until the total area of first portion 134 has been scanned as depicted in FIG. 4B.

Based on this operation, cells 135, 136, 138, 139 are detected. These cells, again, may be cancer cells, fetal cells, bacteria or other cells for which fluorescence markers, quantum dots, DNA nano-particle probes or other marking processes have caused the cells to be identified. The cells, for example, may also be those of other organs of a body, such as liver cells, brain cells, for which markers are developed. Once the translation stage has moved sample 12" to the position noted in FIG. 4B, translation stage 20' is moved in the x-direction (arrow 140) indexing the sample such that a second portion 142 of the sample is under the input aperture of first end 42", as shown in FIG. 4B. Thereafter, translation stage 20' is moved in the direction shown by arrow 144 to scan the second portion 142. It is to be appreciated that while one particular scanning sequence is shown, other sequences may be used. A slight overlap may exist between the first portion 134 and second portion 142 to ensure scanning of the entire sample. Position data is maintained by known indexing or registration processes as previously discussed. Also, while FIGS. 4A-4C show only a first portion 134 and a second portion 142, sample 12" may be larger, resulting in additional portions which will be scanned in a similar process.

In some instances the scanned sample will require processing following the identifying and localization of the cells of interest. At this point, the sample may be removed for these additional actions. For example, once the cells are localized, they can be analyzed for genetic defects using conventional analysis tools like fluorescence in situ hybridization (FISH), or by use of an automated fluorescent microscope, as well as by other investigative systems.

Alternatively, in other situations, a benefit will exist to undertake further investigation as part of the imaging system itself. One of these instances is when the sample being investigated requires a higher resolution than may be obtained by the described system. Therefore, the system of the present application includes a further embodiment, wherein, as shown in FIG. 4C, controller 80 provides the location or positional information of the sample cells 135-139 to an automated high-resolution device 146, such as an automated fluorescent microscope. Once the scanning process has been completed (or during the process), the automated high-resolution device 146 is provided with the cell position information and it is activated to move and investigate the cells in greater detail. Movement of automated high-resolution device 146 may be obtained by translation/gearing arrangements that are well known in the art and similar as those previously described herein. This embodiment finds particular application when it is known or highly suspected a certain cell will be found, for example, when a patient is undergoing treatment for cancer. In this scenario, the integration of the high-resolution device 146 will increase the speed of review.

In the preceding discussion it may be considered that a single type of marker was provided on sample 12", such as one that will attach to one particular type of cancer cell. However, alternative embodiments of the present system include providing the biological smear 14" of sample 12" with a plurality of markers which will attach to different cells of characteristics of a cell type, and which react at distinctly different frequencies of light. Therefore, in one embodiment, sample 12" may include markers which are intended to identify different types of cancer cells (e.g., brain cancer, colon cancer, lung cancer, etc.). Techniques for use of multiple markers is more fully described in U.S. Ser. No. 10/271,347, which has been fully incorporated by reference.

As mentioned in the preceding discussion, a benefit is obtained by providing a first scanning operation under the FAST scan system as described in connection with FIGS. 1-3. In some instances, this is the entire process which will be required. However, in other applications, the use of the FAST scan process is beneficial in obtaining candidate rare cells to be further investigated by a high resolution viewing device, such as a fluorescent microscope. Such a device may be incorporated into the FAST scan system, wherein the sample 12" (or 12) is moved directly to the higher resolution viewing device as described in connection with FIG. 4C. Alternatively, the higher resolution device might be found at a separate location, and therefore, the sample 12" (12) will be physically moved for further investigation. An important aspect of such investigation, both for the FAST scan process and the high resolution investigation, is to identify the location of the detected candidate rare cells within the biological smear 14".

Figure 5:
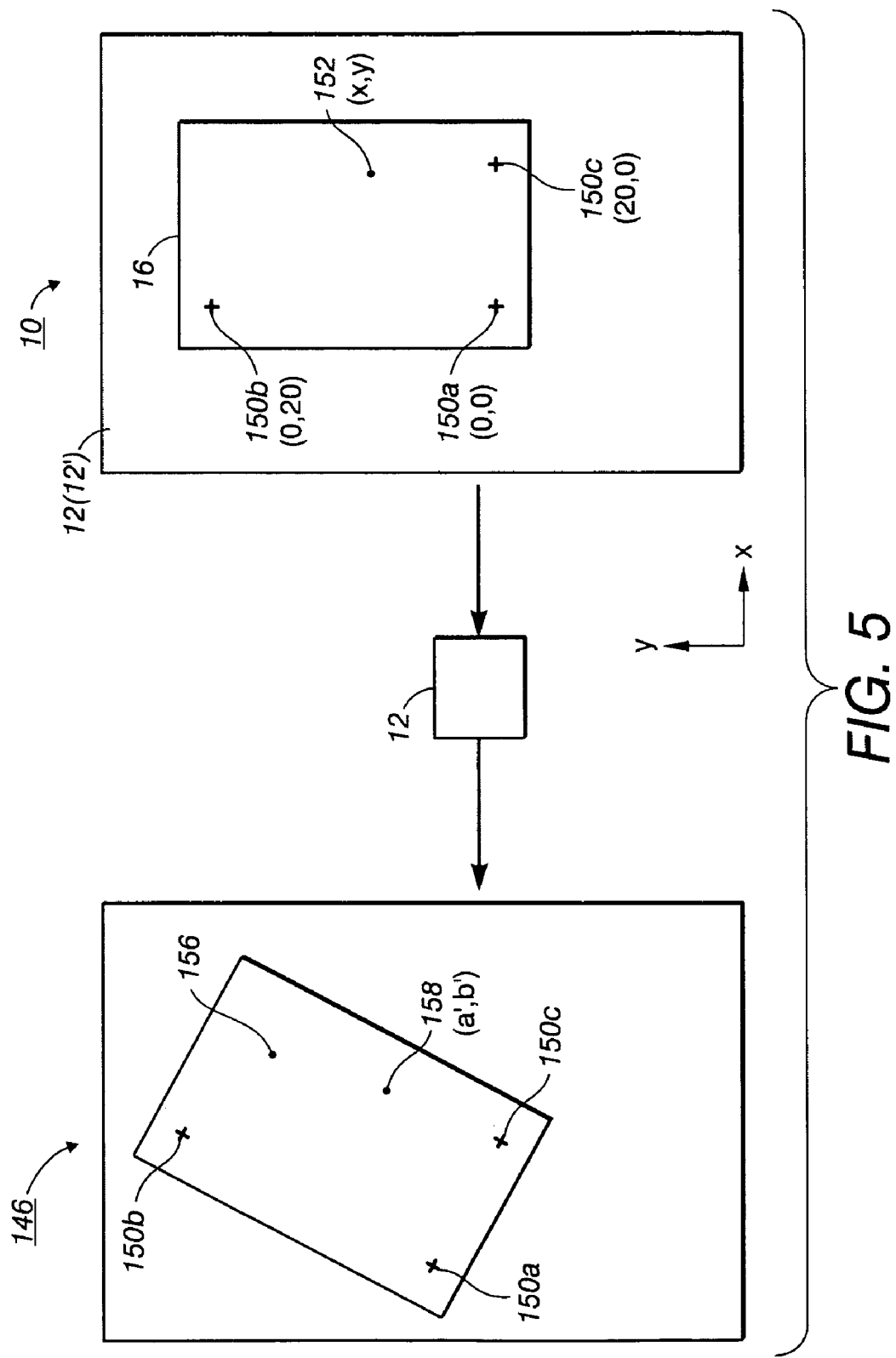
FIG. 5 illustrates issues related to transferring data between two coordinate spaces conveyor-type process for scanning in accordance with the present application.

To more particularly illustrate the problem of transferring data between imaging systems which have unique and distinct coordinate spaces, attention is directed to FIG. 5. For example, the first imaging system such as the FAST scan system 10 employs registration (reticle) marks physically located on a slide 16 of sample 12. The reticle marks include an origin reticle mark 150a, a y-axis reticle mark 150b, and an x-axis reticle mark 150c. These marks are arranged approximately at the vertexes of a right triangle. The FAST scan system 10 will then perform its scanning operation and detect an object 152 (e.g., a candidate rare cell). Thereafter, the positional information of the reticle marks 150a-150c and of the object 152 are obtained. For example, the object 152 may be determined to be at a position (a,b) in this first coordinate space. Following the operation, the sample 12 is transferred to a high resolution system such as the microscope 146 of FIG. 4C. During this transfer to a second coordinate space, the sample 12 may become rotated, presented in a different scale, shifted, skewed, or otherwise affected by the transfer. For example, image skew can arise when one or both of the image scanning systems have their physical scanning directions not accurately perpendicular. Due to this situation, if the coordinates (a,b) are transferred with the sample 12, the user, or automated system, will move an x-y translation stage of the high resolution device to acquire an image of object 152 at an expected position 156. However, due to the above-noted transfer issues, the actual location of object 152 would be at position a', b', thereby making it extremely difficult if not impossible to identify and locate the candidate rare cells. Position a', b' is designated by 158. This location occurs when the coordinate transformation algorithms are applied to coordinates a,b.

The discussion set forth in connection with the following FIGS. 6-12 provides exemplary embodiments which improve the ability of a user to acquire data in the first coordinate space and use that data to accurately transfer the coordinates of selected objects for viewing in a second coordinate space.

In one exemplary embodiment described is a process and system to convert rare cell scanner image coordinates to high resolution device (e.g., microscope) coordinates using the registration (reticle) marks on the samples. The converting operation is a linear procedure, which includes converting known non-linear imperfections. A generalized operational flow of this process is shown by flowchart 160 of FIG. 6. In step 162, a sample including reticle marks and a biological smear is loaded into a rare cell scanning system such as the FAST scan system of FIGS. 1-3. Operation of the FAST scan system causes an image to be generated, including the reticle marks and candidate rare cells. Operation of the system at this point generates positional information of the identified candidate rare cells, as well as position information for the origin and x,y reticles of the sample 164. Optionally, the generated image may be stored as a rare cell (also called sample) image file for later use.

Next, a user institutes a coordinate conversion procedure 166 to begin the process of converting the image data information from the scanner coordinate space into the high resolution coordinate space. In one embodiment, the coordinate conversion procedure of step 166 is implemented as a piece of software on a computing device, having an interface which permits the user to interact with the conversion process. In step 168, the locations for the sample's origin and x,y reticle marks in the image pixel space of the scanner coordinate space are designated.

The sample or rare cell image file is transferred from the FAST scan system to the high resolution device, i.e., microscope, 170. Once the transfer has occurred, known position detecting operations for the high resolution device designate locations of the origin and x,y reticle marks of the sample within the high resolution device coordinate space 172.

The FAST scan process, now computes coordinate conversion parameters for conversion from the scanner coordinate space to the high resolution device coordinate space. Particularly, the system determines any offset shifting in the x- and y-axes, rotation, skew or other positional differences of the sample in the scanner coordinate space location and the high resolution coordinate space 174. Using the information from the scanner coordinate space, the locations of candidate rare cells are designated 176. This information is input into the FAST scanner coordinate conversion process. Thereafter, the system applies coordinate conversion parameters previously determined in step 174 to convert the scanner coordinates to high resolution device coordinates 178. Using this information, the high resolution device x-y stage is translated to the corresponding microscope coordinates of the suspected rare cells 180.

Steps 176-180 may be repeated for a plurality of candidate rare cells. Alternatively, the process may be designed where a plurality of locations in step 176 may be designated at one time, and the application of the coordinate conversion process in 178 processes all designated locations. Thereafter, the translation of the microscope stage automatically moves from a first detected location to a next detected location without a requirement of designating locations of candidate rare cells one at a time.

Figure 6:
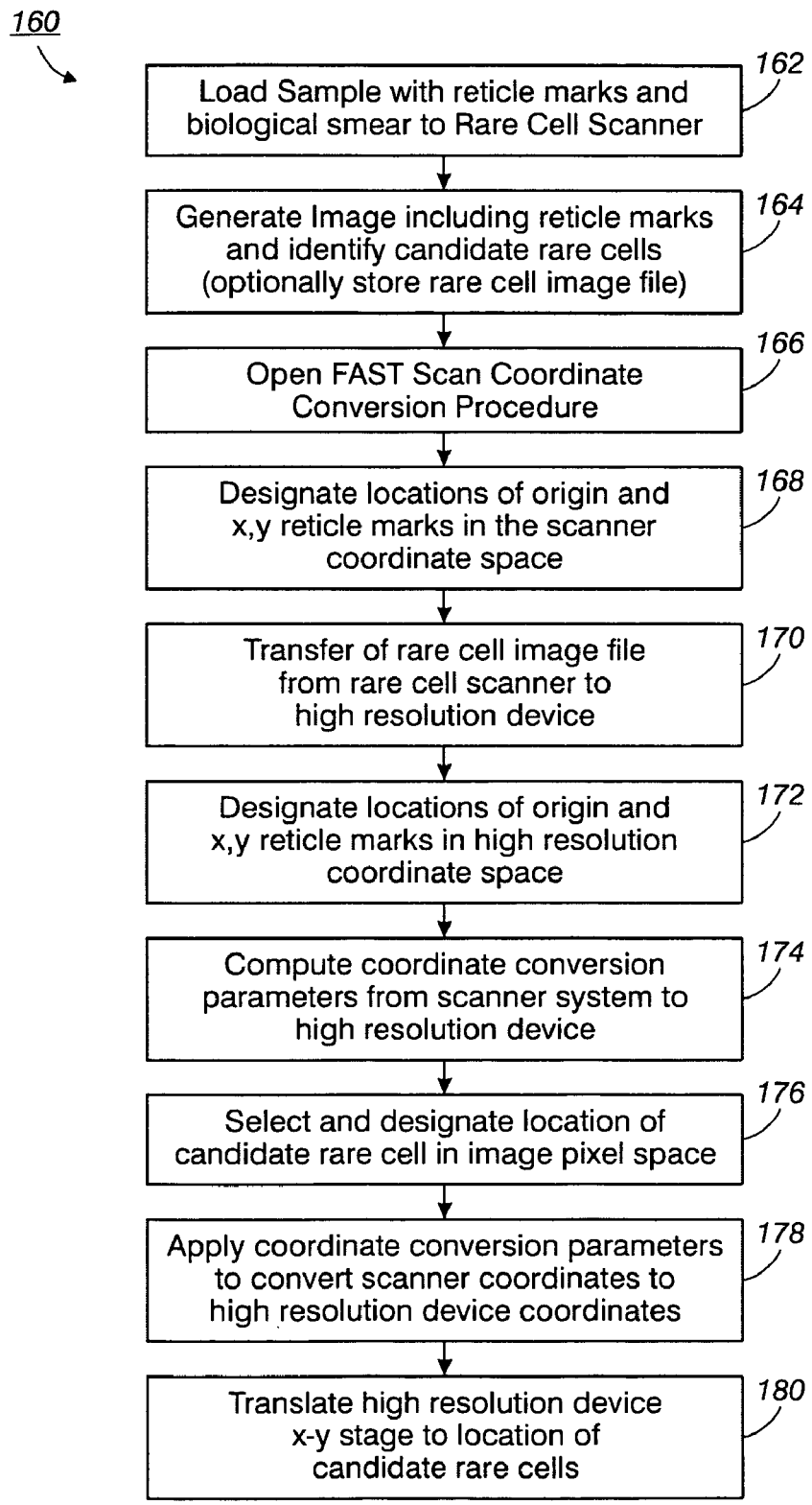
FIG. 6 illustrates a flow chart showing the general process of transferring potential rare cells from a scanner coordinate system to a microscope coordinate system.
Figure 7:
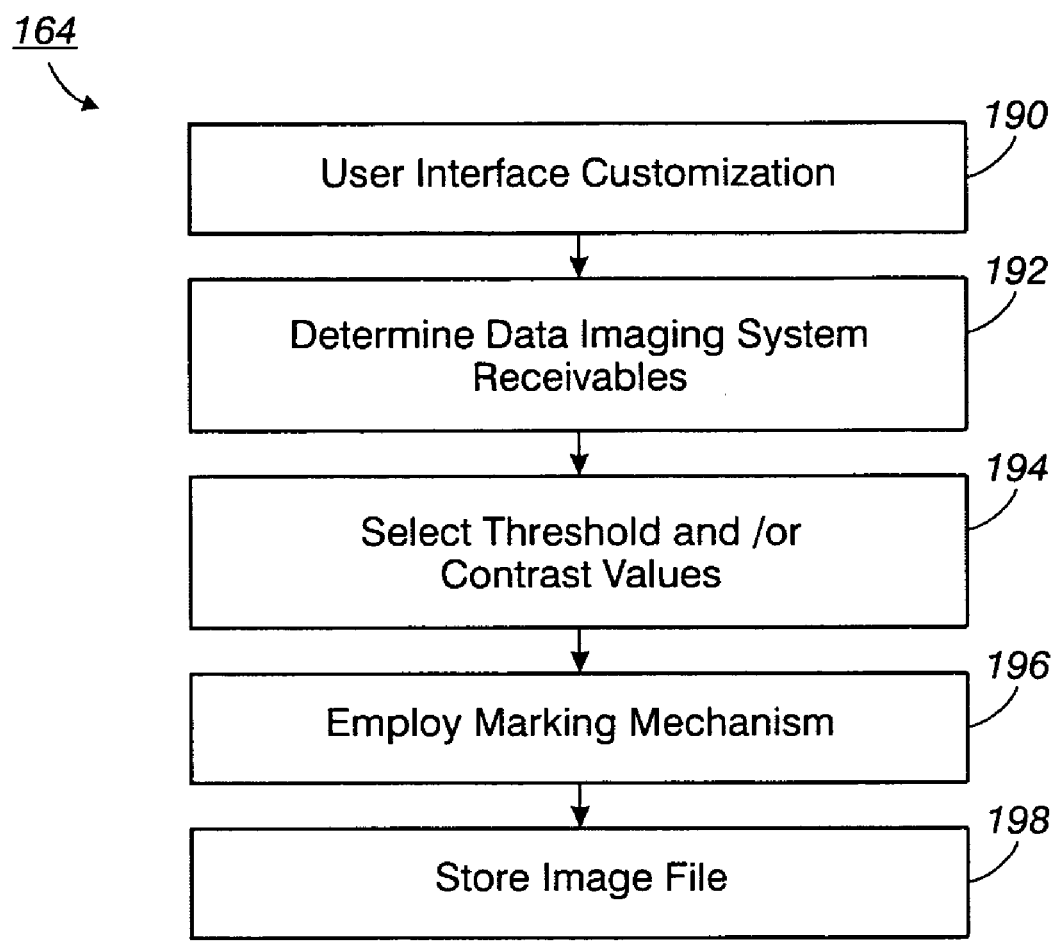
FIG. 7 shows a flow chart for the identification of potential rare cells in the scanner system.

Turning to FIG. 7, illustrated is expanded detail related to step 164 of FIG. 6, which includes the generation of the image of the sample, and the locating of the origin, x,y reticle marks, and candidate rare cells. The user is provided with an interface which permits for the customization of the image 190. In step 192 the user determines the data the system will receive. For example, a determination may be made of the scan rate, and degree of light which may be received by detectors. The user may then determine a threshold and/or contrast of the images to be displayed, step 194. Once the images are displayed, the user is provided with a marking mechanism, 196 whereby images of candidate rare cells of interest may be electronically marked. In step 198, the user has the option of storing the image as an image file for later review, and/or use in the high resolution viewing operation.

Figure 8:
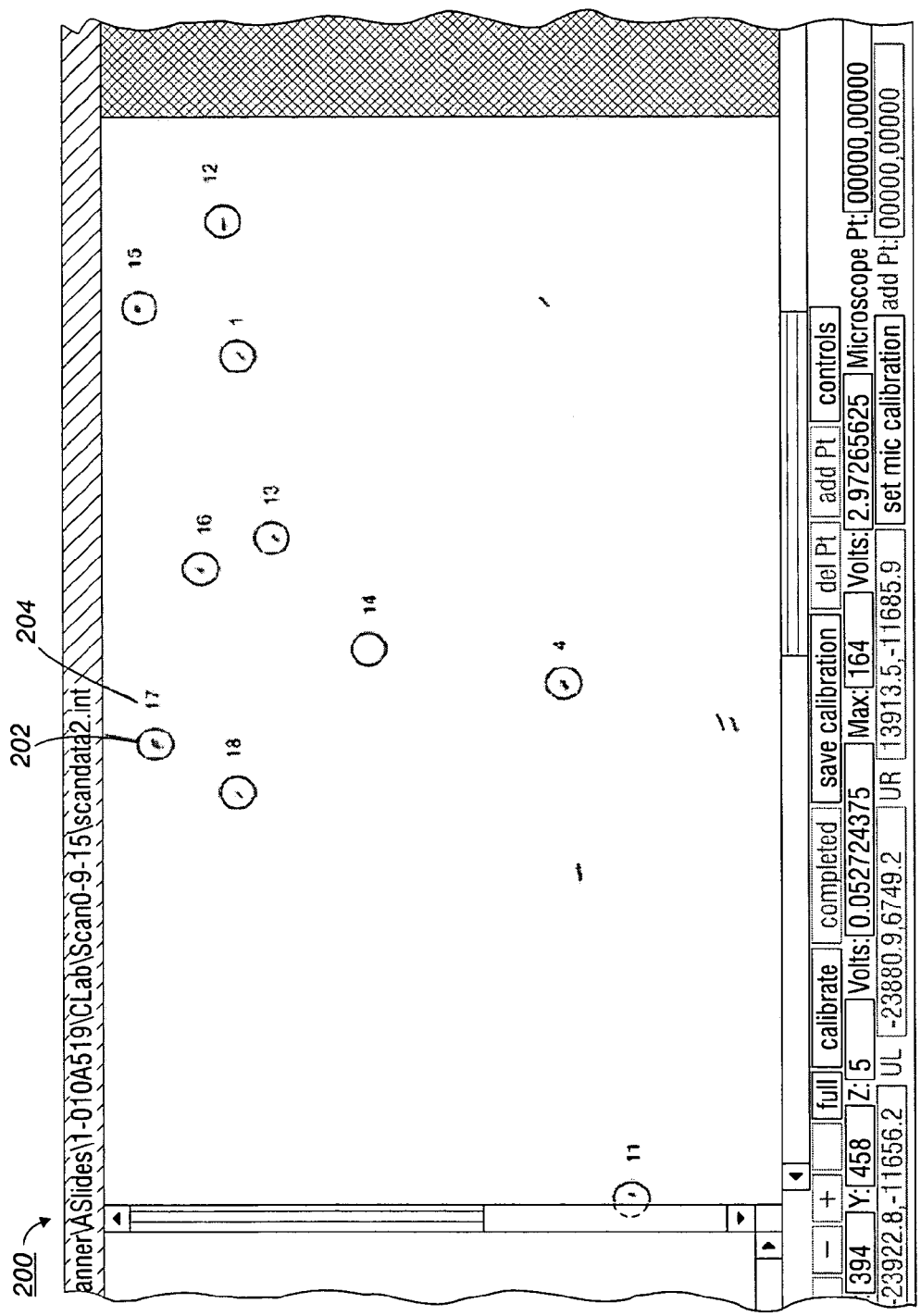
FIG. 8 illustrates identified potential rare cells with a surrounding control box.
Figure 9:
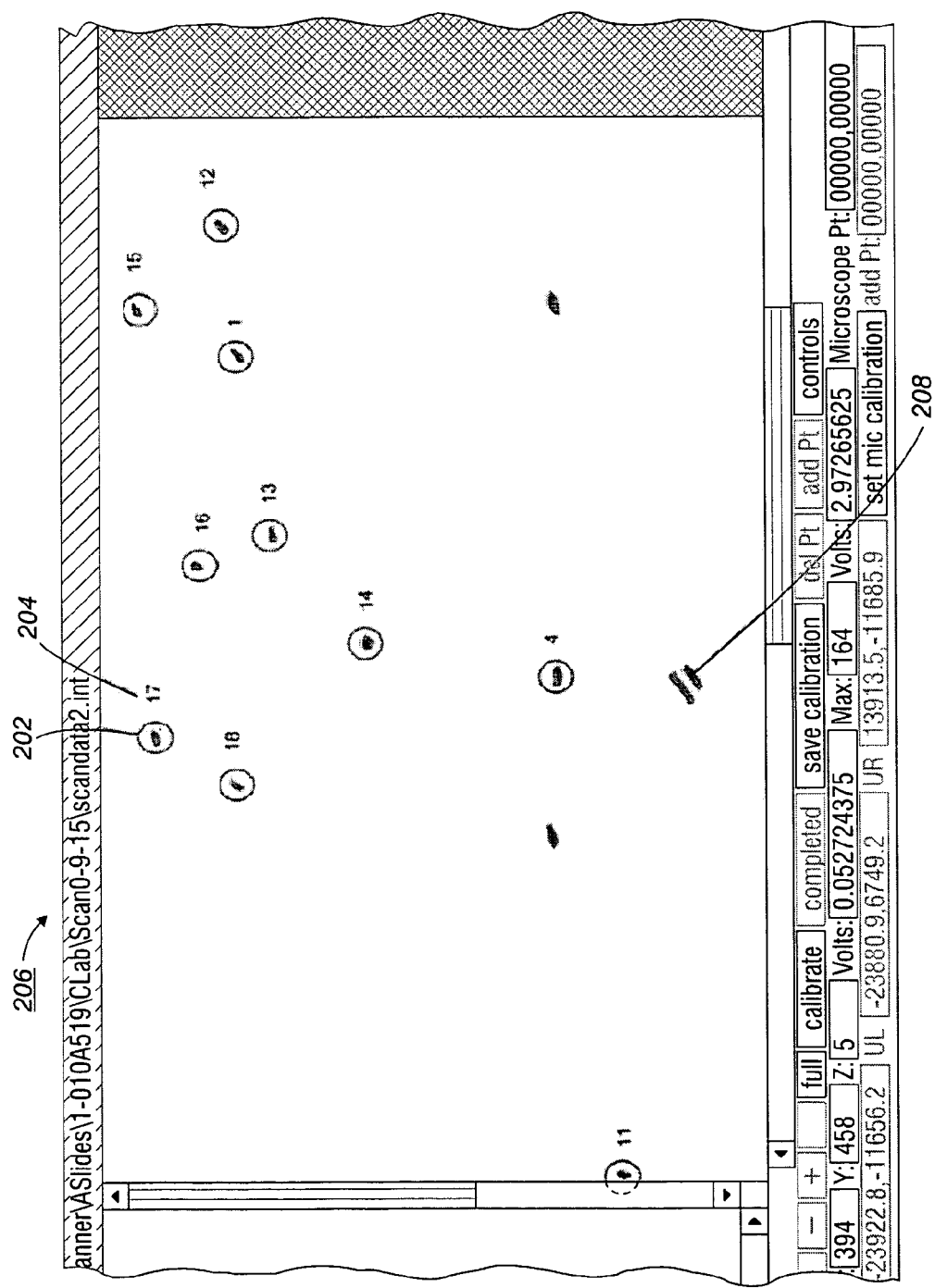
FIG. 9 identifies additional potential rare cells with a surrounding control box.

FIGS. 8 and 9 illustrate exemplary images of displayed candidate rare cells of interest, where the image has been generated in accordance with the FAST scanner system of FIGS. 1-3. FIG. 8 shows an image 200 where a user has identified a variety of cells and has used a marking mechanism, i.e., such as a mouse or other known pointing and marking mechanism. The system generates a circle 202 around a cell of interest, and also attaches an associated number to further identify that cell. Of interest, in one embodiment, the user may use a color coding of the numbers and/or circles. For example, cells 1, 13 and 15-18 may in this embodiment be designated with a red circles, cells 4 and 12 are designated with the green circles, and cell 14 is designated with the color blue. The colors may represent any identifying characteristic. In one example, red may be of highest interest, green of a secondary, and blue of least interest. Of course, this is not to be limited to this embodiment, but any appropriate use of the color designations may be employed to further accelerate the process and/or to provide an increased reliability in the process.

Turning to FIG. 9, shown is a second image 206 similar to the first. The main distinction in this is to show the effects of increasing a contrast level, whereby more intense light is generated by the fluorescent coupling. It may be noted, near the bottom of the page, objects 208 have not been designated for further investigation. Specifically, this is another thresholding of cells in that it may be determined by the user by visual representation. For example, the potential cells in this situation may be in too large a cluster, indicating to the user that, rather than candidate rare cells, they are dirt or other impediments in the sample. With this knowledge, the user may disregard further investigation.

Figure 10:
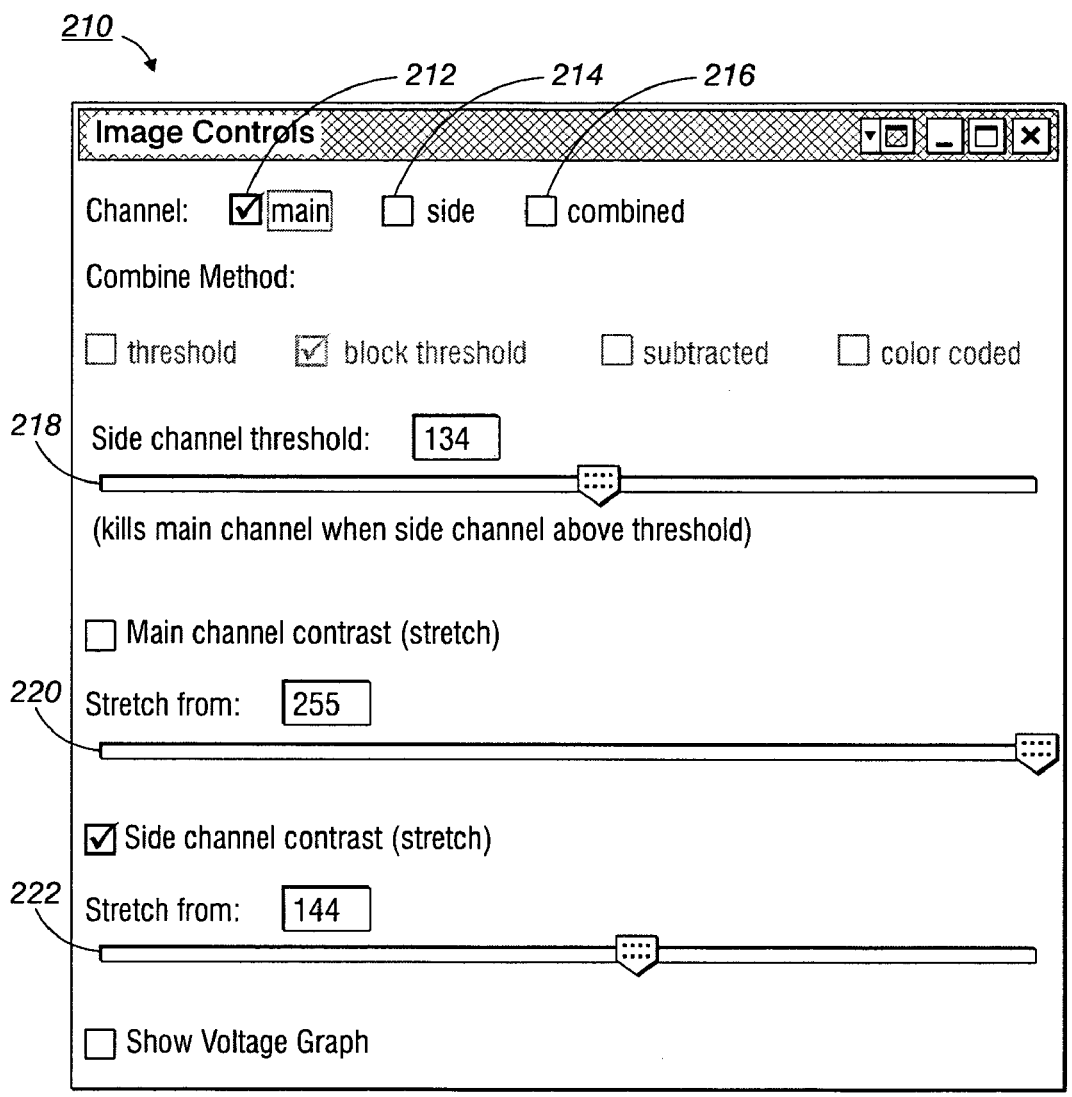
FIG. 10 depicts an additional control box for operation of the system of the flow chart of FIG. 7.

Turning to FIG. 10, illustrated is a front of a user interface 210 which may be used in the interface control system of FIG. 7. Particularly, the user may select from where light is acquired, i.e., a main channel, a side channel or a combination of the two, 212, 214, 216. Slide bars are also provided 218, 220, and 222 to give the user the ability to customize the returned images dependant upon selected threshold and contrast levels, among other items. Intensity, size, two channel intensity ratio, etc., are other characteristics for which controls may be developed.

Once the image has been detected and stored, the image file (i.e., image of sample) can be saved as in step 198 of FIG. 7. This image file (e.g., rare cell image file) is then available for use in the microscope system FIGS. 11A-11D and the associated description set forth a coordinate conversion system 230 which may be used to convert first coordinates, such as rare cell scanner image coordinates to second coordinates, such as microscope coordinates. It is to be understood, however, that the described process is also applicable to other applications where image data is transferred between imaging systems having distinct coordinate spaces.

The coordinate conversion system 230 includes a variety of input and output blocks, whose functions will be described in greater detail below. At the top of FIG. 1, shown is Scanner Input block 232, Scanner Parameter blocks 234, 236, Microscope Input block 238 and Microscope Parameter blocks 240, 242, 244. A lower portion of the coordinate conversion system 230 includes a scanner IMAGE Hit Data block 246, Shifted Scanner Coordinates block 248 and Rotated Scanner Coordinates block 250. Further included is an Independent Coordinates block 252 configured to receive data from the previous blocks. Thereafter, data from Independent Coordinates block 252 is used by microscope blocks, including Skewed & Scaled 'Scope Coordinates block 254, and Rotated Microscope Coordinates block 256, which function to generate positional data for converted microscope coordinates block 258. It may be understood the first three rows under the aforementioned block components 246-258 are provided for visual verification of the proper operation of the system. Particularly, the values inserted within the Input block 232 will be the same values of the first three rows of the IMAGE Hit Data block 246. Thereafter, when all parameters and values have been entered, and the system performs its operations, the data in the first three rows of the converted M-SCOPE Coordinates block 258 will be the same as those in the Microscope Input block 238, confirming proper transformation operations.

Inputs 260 and 262, of the IMAGE Hit Data block 246 permit a user to enter location data in the scanner workspace, which then, through operation of the system, generates positional data in the microscope coordinate space. The details of this operation will be expanded upon in the following paragraphs.

Figure 11A:
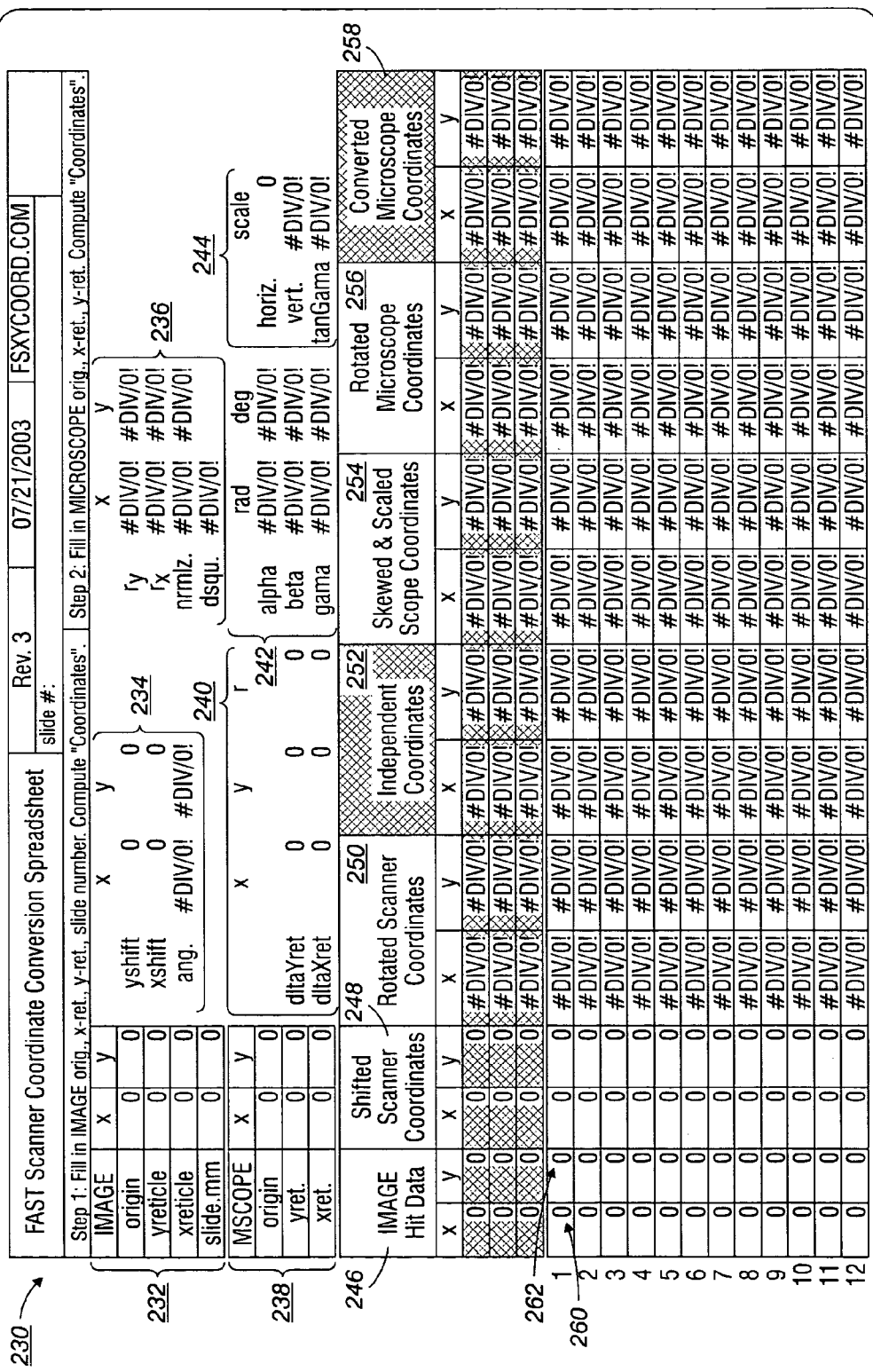

It is to be appreciated the particular arrangement of components, as illustrated in FIG. 11A, are not intended to be a limiting factor as to the concepts of these exemplary embodiments. Rather, the system may be designed in different arrangements from FIG. 11A, and even the representation of FIG. 11A may be altered. For example, the verification rows (i.e., the first three rows under the discussed blocks 246-258) do not need to be shown.

With continuing reference to FIG. 11A, no values have been entered into the coordinate conversion system 230. However, input block 232 is designed to accept x and y coordinates (values) obtained from the rare cell scanner for, (i) the origin reticle (origin), (ii) the y-reticle (yreticle), (iii) the x-reticle (xreticle), and (iv) the size of the sample (slide.mm). Upon insertion of this information, the coordinate conversion system 230 generates parameter values to convert the rare cell scanner position information of input block 232 into position information of an independent coordinate system. Particularly, in block 234, the parameters to identify any shifting in the x and y position of the sample in the scanner-based coordinates space are found by:

(1) yshift(x)=yreticle x–origin x, (2) yshift–(y)=yreticle y–origin y, (3) xshift(x)=xreticle x–origin x, and (4) xshift(y)=xreticle y–origin y, (e.g., –10,1250, –390, 10 of block 234).

An angle the sample may have shifted is found, in radians, by:

(5) ang=–A TAN2(xshft x,xshft y), (e.g., –3.11596 of block 234), and the radian angle shift is then converted to degrees via:

(6) ang=DEGREES(ang), (e.g., –178.531 of block 234).

Rotation parameters for the x- and y-reticles along with the normalization of the angle ("nrmlz") and any de-skewing ("dsqu") of the sample in the scanner system are provided through the parameters in block 236. These parameters define rotation of the y-reticle in the x-direction (ry(x)) and in the y-direction (ry(y)) by:

(7) ry(x)=yreticle x–origin x*(COS(ang))–yreticle y–origin y*(SIN(ang)), and (8) ry(y)=yreticle x–origin x*(SIN(ang))+yreticle y–origin y*(COS(ang)), (e.g., 42.03747, –1249.33 of block 236).

Rotation of the x-reticle in the x-direction (rx(x)) and in the direction (rx(y)) is found by:

(9) rx(x)=xreticle x–origin x*(COS(ang))–xreticle y–origin y*SIN(ang)), and

(10) rx(y)=xreticle x–origin x*(SIN(ang))+xreticle y–origin y*(COS(ang)), (e.g., 390.1282, 1.21E-13 of block 236).

Determining the normalization (nrmlz) of the sample (slide.mm) in the x-direction is determined by:

(11) nrmlz(x)=slide.mm x/rx 'x', and normalization of the slide in the y-direction is found by:

(12) nrmlz(y)=–slide.mm y/ry 'y', (e.g., 0.097404, 0.014808 of block 236).

Once the above parameters values are determined, they are used throughout repeated operations of the coordinate conversion system 230 for values input at inputs 260, 262. De-skewing of the sample is determined by:

(13) dsqu(x)=ry 'x'/ry 'y', (e.g., −0.03365 of block 236).

Figure 11B:
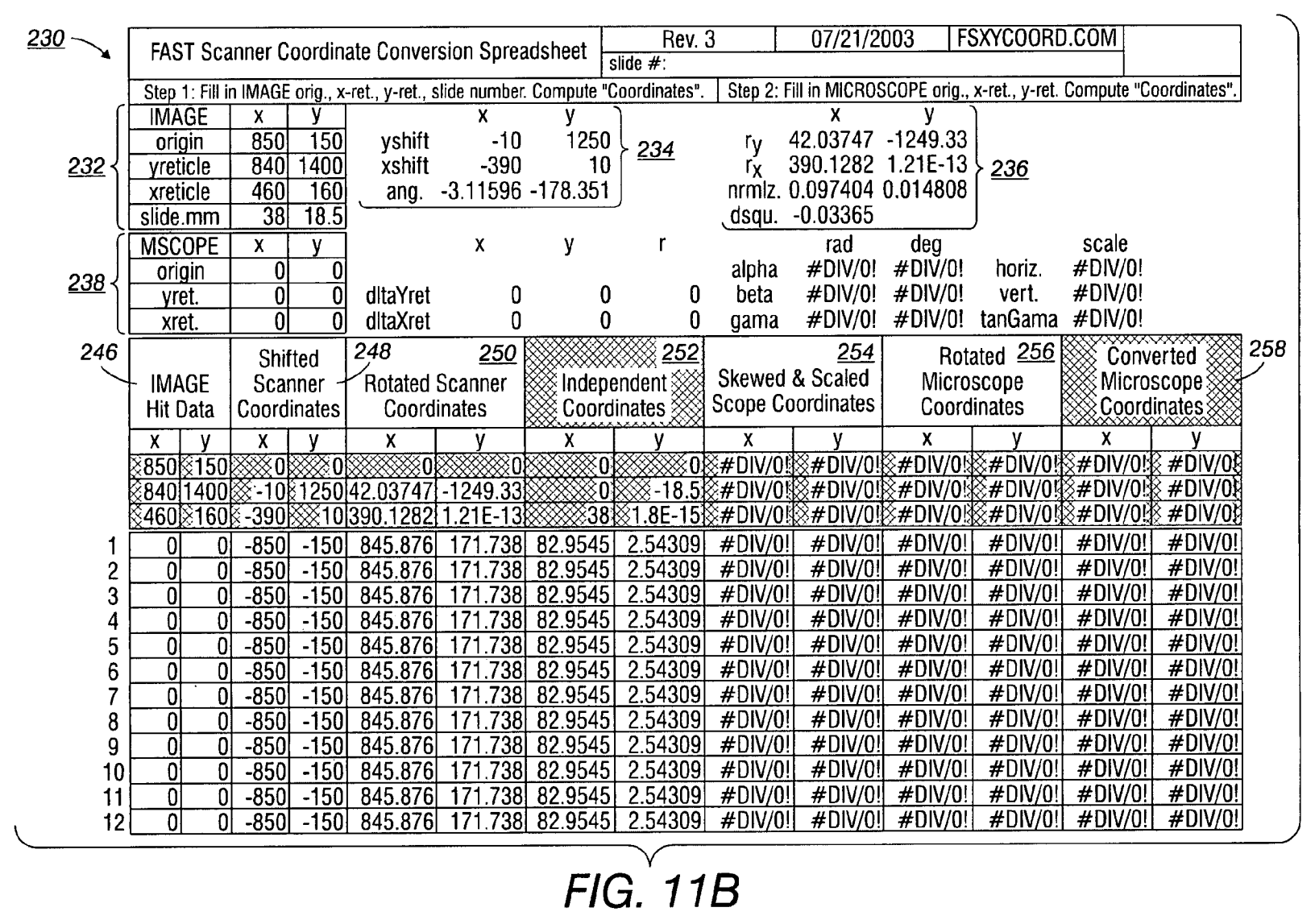

As evidenced in FIG. 11B, when specific values (e.g., origin(x)=850, origin(y)=150, etc.) are entered to input block 232, the system generates parameter values (e.g., yshift(x)=−10, yshift(y)=1250) for the transformation of coordinates in the scanner space to the independent coordinate space. Looking at IMAGE Hit Data block 246, the x and y position data (values) are the same as that of input block 232 (e.g., 850, 150, etc.), which defines where the reticles are located within the scanner coordinate space. Shifted Scanner Coordinates block 248 displays whether the sample in the scanner system (10 of FIG. 1) has been shifted. This information is obtained, by use of the previously described parameters. More specifically, determination of shifted scanner coordinates (shift-scan) for the x and y positions of the origin reticle (origin) are determined by:

(14) shift-scan origin(x)=origin x−origin x, and
(15) shift-scan origin(y)=origin y−origin y, (e.g., 0, 0 first row of block 248).

To determine whether any shifting occurred for the y-reticle, the following relationships are used:

(16) shift-scan y-reticle(x)=yreticle x−origin x, and
(17) shift-scan y-reticle(y)=yreticle y−origin y, (e.g., −10, 1250 second row of block 248).

Similarly, shifting of the x-reticle is found by:

(18) shift-scan x-reticle(x)=xreticle x−origin x, and
(19) shift-scan x-reticle(y)=xreticle y−origin y, (e.g., −390, 10 third row of block 248).

In Rotated Scanner Coordinates block 250, rotation of the sample while in the scanner coordinate system (rotate-scan), is determined for the origin reticle (origin) in the x and y-directions by:

(20) rotate-scan origin(x)=shift-scan origin (x)*(COS(ang))−shift-scan origin (y)*(SIN(ang)),
(21) rotate-scan origin(y)=shift-scan origin(−x)*(SIN(ang))+shift-scan origin(y)*(COS(ang)), (e.g., 0, 0 in first row of block 250), and for the y-reticle in the x and y-directions by:

(22) rotate-scan y-reticle(x)=shift-scan y-reticle(x)*(COS(ang))−shift-scan y-reticle(y)*(SIN(ang)),
(23) rotate-scan y-reticle(y)=shift-scan y-reticle(x)*(SIN(ang))+shift-scan y-reticle(y)*(COS(ang)) (e.g., 42.03747,−1249.33 in second row of block 250), and for the x-reticle in the x and y-directions by:

(24) rotate-scan x-reticle(x)=shift-scan x-reticle(x)*(COS(ang))−shift-scan x-reticle(y)*(SIN(ang)),
(25) rotate-scan x-reticle(y)=shift-scan x-reticle(x)*(SIN(ang))+shift-scan x-reticle(y)*(COS(ang)) (e.g., 390.1282, 1.21E-13 in third row of block 250).

Having determined values for the parameters of blocks 234 and 236, along with the position of any Shifted Scanner Coordinates 248 or Rotated Scanner Coordinates 250, the system is then able to develop independent coordinate positioning (inde-scan) as set forth in Independent Coordinates block 252, using the following relationships. Particularly, the origin reticle (origin) in the x and y-directions, in the independent coordinate space, is found by:

(26) inde-scan origin(x)=(rotate-scan origin(x)−(dsqu*rotate-scan origin(y))*nrmlz 'x',
(27) inde-scan origin(y)=rotate-scan origin(y)*nrmlz 'y' (e.g., 0, 0 in first row of block 252), and for the y-reticle, in the x and y-directions is found by:

(28) inde-scan y-reticle(x)=(rotate-scan y-reticle(x)−(dsqu*rotate-scan y-reticle(y))*nrmlz 'x',
(29) inde-scan y-reticle(y)=rotate-scan y-reticle(y)*nrmlz 'y' (e.g., 0, −18.5 in second row of block 252), and for the x-reticle, in the x and y-directions is found by:

(30) inde-scan x-reticle(x)=rotate-scan x-reticle(x)−(dsqu*rotate-scan x-reticle(y))*nrmlz 'x',
(31) inde-scan x-reticle(y)=rotate-scan x-reticle(y)*nrmlz 'y', (e.g., 38, 1.79E-15 in third row of block 252).

The preceding operations develop coordinate values for the independent coordinate space (i.e., Independent Coordinates block 252), disassociated from the scanner coordinate space. This design permits these independent coordinates to then be transformed into the microscope coordinate space. As may be observed in FIG. 11B, input area 238 has not yet been provided with designated locations of the origin, and the x and y reticles of the microscope coordinate space. Once this information is provided, the system will then use the independent coordinate information of block 252 as a starting point, and generate Skewed and Scaled Microscope Coordinates in (i.e., block 254), and Rotated Microscope Coordinates (i.e., block 256) and shifted (i.e., block 258) to generate microscope coordinate parameters for Converted Microscope Coordinates block 258.

Note that in independent space, the coordinates of the reticles are exactly perpendicular to each other, have the perfect size, and have no shift. These properties are not necessarily present in either the input space or the output space.

Figure 11C:
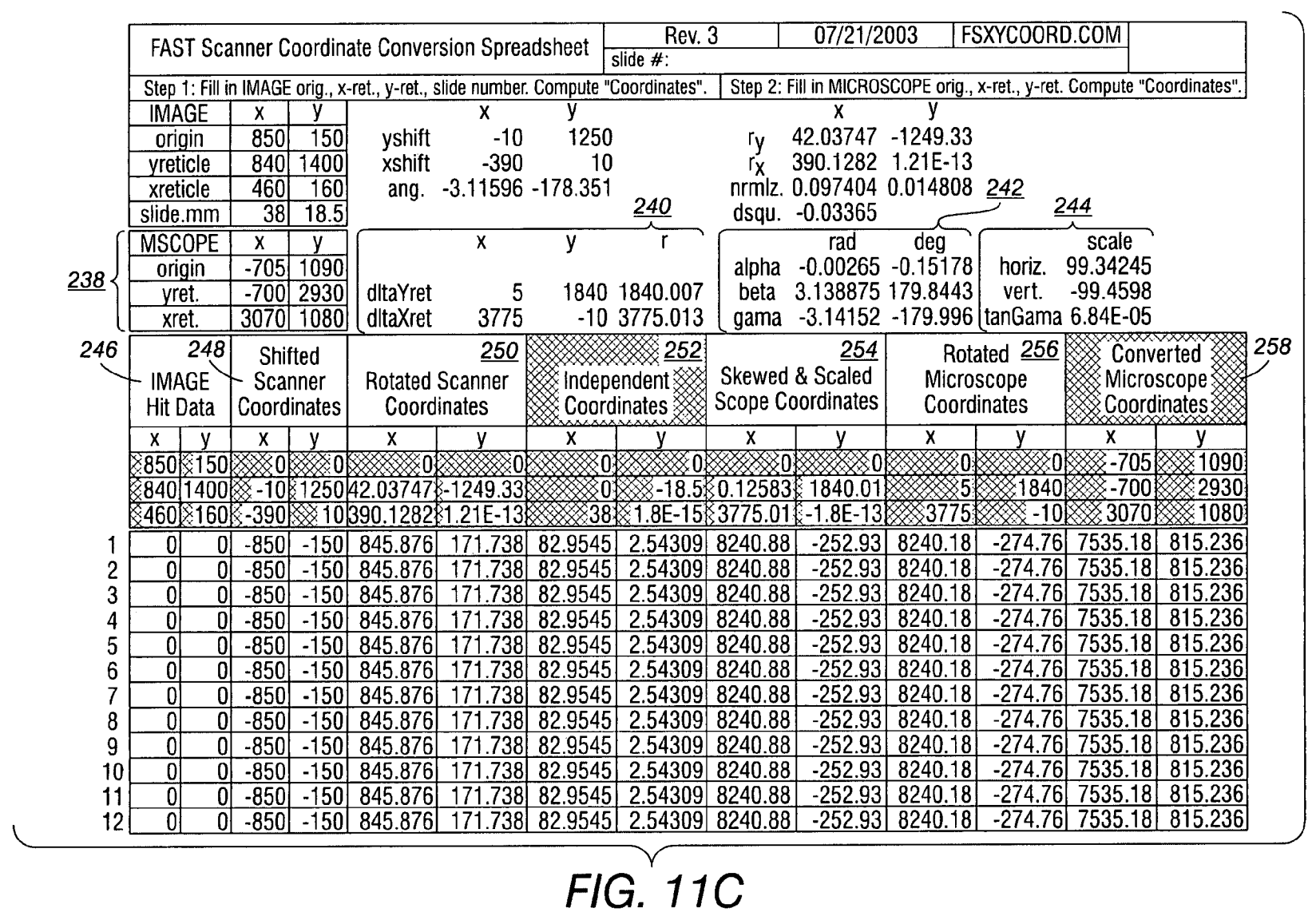

Turning to FIG. 11C, an input block is provided to accept x and y coordinates obtained from the microscope system for the origin reticle (origin), y reticle (yreticle), x-reticle (xreticle, and the size of the sample (slide.mm). Using this information, the formulas of parameter set 240 are used to determine the delta-y reticle (dltaYret) in the x, y-directions and the hypotenuse of the angle (r) by solving:

(32) dltaYret (x)=(yret x)−(orig x),
(33) ditaYret (y)=(yret y)−(orig y),
(34) ditaYret (r)=SQRT(SUMSQ(dltaYret x,dltaYret y)), (e.g., 5, 1840, 1840.007, of block 240), and solving for the delta-x reticle (dltaXret) by:

(35) dltaXret (x)=(xret x)−(orig x),
(36) dltaXret (y)=(yret y)−(orig y),
(37) dltaXret (r)=SQRT(SUMSQ(dltaXret x,dltaYret y)), (e.g., 3775, −10, 3775.013 of block 240).

Thereafter, the alpha, beta and gamma values, which are the line angles formed by the origin, y-reticle and x-reticle, in radians and degrees, are found by:

(38) alpha(rad)=A TAN2(dltaXret x,dltaXret y),
(39) alpha(deg)=DEGREES(atpha rad),
(40) beta(rad)=0.5*π(−)+A TAN2(dltaYret x, dltaYret y),
(41) beta(deg)=DEGREES(beta rad),
(42) gama(rad)=(alpha rad)−(beta rad), and
(43) gama (deg)=DEGREES('gama' rad), (e.g., −0.00265, −0.15178, 3.138875, 179.8443, −3.14152, −179.996 of block 242)), where dltaXret represents the delta of the x-reticle, and dltaYret represents the delta of the y-reticle.

With further attention to the parameters, horizontal (horiz scale), vertical (vert scale) and tan Gama (tan Gama scale) scaling of the sample for the microscope coordinate conversion are found by:

(44) horiz scale=(dltaXret 'r')/slide.mmX,
(45) vert scale=(dltaYret 'r')*CQS('gama' rad )/slide.mmY, and

(46) tan Gama scale=TAN('gama' rad), (e.g., 99.34245, −99.4598, 6.84E−05 of block 244).

With continuing attention to FIG. 11C, by insertion of the values into the microscope input section 238, corresponding parameters to be used for the conversion of specific coordinate points of the independent coordinate space may now be obtained for the transfer microscope coordinate space.

Using this information, the system then develops values for skewed and scaled microscope coordinates of the Skewed & Scaled 'Scope Coordinates block 254, rotated microscope coordinates in Rotated Microscope Coordinates block 256, and the shifted microscope coordinate parameters in Converted M-Scope Coordinates block 258.

With attention to block 254, the skewed and scaled microscope coordinates (sk/scl-scope), of the sample, to be used in the coordinate transformation process are found for the origin reticle in x and y-directions by:

(47) sk/scl-scope origin(x)=(inde-scan origin(x)*horiz scale+inde-scan origin(y)*(vert scale)*(tan Gama scale)),

(48) sk/scl-scope orig in(y)=inde-scan origin(y)*(vert scale), (e.g., 0, 0 in first row of block 254), and for the x and y-directions for y-reticle by:

(49) sk/scl-scope y-reticle(x)=inde-scan y-reticle(x)*(horiz scale)+(inde-scan y-reticle(y)*(vert scale)*(tan Gama scale)),

(50) sk/scl-scope y-reticle(y)=inde-scan y-reticle(y)*(vert scale), (e.g., 0.12583, 1840.01 of second row of block 254), and for the x and y-directions for x-reticle by:

(51) sk/scl-scope x-reticle(x)=inde-scan x-reticle(x)*(horiz scale)+(inde-scan x-reticle(y)*(vert scale)*(tan Gama scale)),

(52) sk/scl-scope x-reticle(y)=inde-scan x-reticle(y)*(vert scale), (e.g., 3775.01, −1.8E−13 of third row of block 254).

To determine rotation of the sample in the microscope coordinate space, (rotate-scope) (block 256) the following formulas are applied, where the origin reticle in the x and y-directions are found by:

(53) rotate-scope orig in(x)=sk/scl-scope origin(x)*(COS(alpha rad))sk/scl-scope origin(y)*(SIN(alpha rad)),

(54) rotate-scope origin(y)=sk/scl-scope origin(x)*(SIN(alpha rad))+sk/scl-scope origin(y)*(COS(alpha rad)) (e.g., 0, 0 first row of block 256), and for x and y-directions of the y-reticle:

(55) rotate-scope y-reticle(x)=sk/scl-scope y-reticle(x)*(COS(alpha rad))−sk/scl-scope y-reticle(y)*(SIN(alpha rad)),

(56) rotate-scope y-reticle(y)=sk/scl-scope y-reticle(x)*(SIN(alpha rad ))+sk/scl-scope y-reticle(y)*(COS(alpha rad)), (e.g., 5, 1840 of second row of block 256), and finally for x and y-directions of the x-reticle:

(57) rotate-scope x-reticle(x)=sk/scl-scope x-reticle(x)*(COS(alpha rad)−sk/scl-scope x-reticle(y)*(SIN(alpha rad)),

(58) rotate-scope x-reticle(y)=sk/scl-scope x-reticle(x)*(SIN(alpha rad ))+sk/scl-scope x-reticle(y)*(COS(alpha rad)), (e.g., 3775, −10 of third row of block 256).

Using this data, the converted microscope coordinate parameters (convert-scope) (block 258) for the x and y-directions may be obtained for the origin reticle in the x and y-directions by:

(59) convert-scope origin(x)=rotate-scope origin(x)+(orig x),

(60) convert-scope origin(y)=rotate-scope origin(y)+(orig y), (e.g., −705, 1090 of first row of block 258), and for x and y-directions of the y-reticle:

(61) convert-scope y-reticle(x)=rotate-scope y-reticle(x)+(orig x),

(62) convert-scope y-reticle(y)=rotate-scope y-reticle(y)+(orig y), (e.g., −700, 2930 of second row of block 258), and for x and y-directions of the x-reticle:

(63) convert-scope x-reticle(x)=rotate-scope x-reticle(x)+(orig x),

(64) convert-scope x-reticle(y)=rotate-scope x-reticle(y)+(orig y), (e.g., 3070, 1080 of third row of block 258).

Having obtained the above coordinate conversion parameters, the user may then input either directly or automatically, rare cell scanner coordinates for objects (e.g., candidate rare cells) such as those shown in FIGS. 9 and 10. The x and y coordinates for these objects are entered into columns 260 and 262 of FIG. 11D, respectively. The system then translates the x and y rare cell scanner coordinates (e.g., x=1000, y=2132) of an object, into independent coordinate space coordinates (e.g., x=−16.1636, y=−29.3966), and thereafter into a microscope coordinate space coordinates (e.g., x=−2302.79, y=4018.019).

The process for achieving conversion for the entered coordinates (e.g., x=1000 and y=2132) values (value(x), value (y)) of an object (object 1−object+n), will now be discussed in more detail. The shifted scanner coordinates (shift-scan) for those values inserted in columns 260 and 262 is by:

(65) shift-scan(object 1)(x)=value(x)−origin x, and

(66) shift-scan(object 1)(y)=value(y−origin y.

Rotated scanner coordinates of the object (rotate-scan) in the x and y-directions are found by:

(67) rotate-scan(object 1)(x)=shift-scan(object 1)(x)*(COS(ang))−shift-scan(object 1)(y)*(SIN(ang)), and

(68) rotate-scan(object 1)(y)=shift-scan(object 1)(x)*(SIN(ang))+shift-scan(object 1)(y)*(COS(ang)).

Using the provided relationship, the independent coordinates (inde-scan) of the entered coordinates—in the x and y-directions are found by:

(69) inde-scan(object 1)(x)=rotate-scan(object 1)(x)−(dsqu*rotate-scan(object 1)(y))*nrmlz 'x', and

(70) inde-scan(object 1)(y)=rotate-scan(object 1)(y)*nrmlz 'y'.

From the obtained independent coordinates, skewed and scaled microscope coordinates (sk/scl-scope) for the x and y coordinates input in columns 260 and 262 are found by:

(71) sk/scl-scope (object 1)(x)=inde-scan(object 1)(x)*horiz scale+(inde-scan(object 1)(y)*(vert scale)*(tan Gama scale)), and

(72) sk/scl-scope (object 1)(y)=inde-scan(object 1)(y)*(vert scale).

Thereafter, the rotated microscope coordinates (rotate-scope) for the x and y values in columns 260 and 262 are determined by:

(73) rotate-scope(object 1)(x)=sk/scl-scope (object 1)(x)*(COS(alpha rad))−sk/scl-scope (object 1)(y)*(SIN(alpha rad)), and

(74) rotate-scope(object 1)(y)=sk/scl-scope (object 1)(x)*(SIN(alpha rad))+sk/scl-scope (object 1)(y)*(COS(alpha rad)).

Lastly, the values from columns 260 and 262 are finally converted into the microscope coordinate space (convert-scope) in the x and y-directions by:

(75) convert-scope(object 1)(x)=rotate-scope(object 1)(x)+ (orig x), and

(76) convert-scope(object 1)(y)=rotate-scope(object 1)(y)+ (orig y).

Thus, the above-described process permits for the transformation of coordinate points in a first coordinate space to coordinate points in a second coordinate space. While the above discussion focused on transformation from a rare cell image scanner to a microscope coordinate space, coordinate conversion system 230 is not limited to this implementation. Rather, the system is considered to teach a generalized planar object position locator process that may be used for conversion between coordinate spaces of distinct imaging systems.

The described system takes advantage of an object holder (e.g., slide/sample) with at least three marks, such as reticle marks, arranged approximately at the vertexes of a right triangle. A first imaging device then defines a first coordinate space, and the coordinates of the reticle marks in the first coordinate space are designated. The sample or image of the sample is then provided to a second imaging device which defines a second coordinate space, and the reticle marks are designated in this second coordinate space. Using these designated coordinates of the reticle marks from the first coordinate space and the second coordinate space, the values for coordinate conversion parameters are computed and used to perform transformation operations. The disclosed mechanism enables two pieces of equipment with different and perhaps imperfect coordinate spaces to work together, even if their scan rates are not perpendicular to their process directions, and even if the object holder is inadvertently rotated, skewed or otherwise mispositioned.

In the above description, the origin reticle and the x-reticle are used to define the horizontal axes, and the origin reticle and the y-reticle are used to define the vertical axes. Of course, this description is not intended to be limited to this design, and other axes arrangements may be used. The described steps were recited to include de-shift, de-rotate and de-skewing the position information of the first coordinate space into the independent coordinate space. The system then skews, rotates and shifts the information of the independent coordinate space into the microscope (or target) coordinate space. These steps do not need to be performed in the order described, and other steps may also be used to determine the position of the sample.

System 230 is sufficiently modularized such that it works in a reverse direction, as shown by FIG. 12. Particularly, the coordinates of an object may be located in the second coordinate space (i.e., the microscope HIT Data block) and by insertion of coordinate Information as previously discussed in connection with FIGS. 11A-11D, the process will convert the information back into coordinates in first coordinate space (i.e., Converted IMAGE Coordinates block).

To more fully explain the modularity of the system, which permits operation in a reverse direction such as in FIG. 12, a comparison between FIG. 11A and 12 will be undertaken. In FIG. 12, the various input blocks have been slightly changed in their identification. Particularly, what might was a "scanner" block will now be identified to hold or generate "microscope" information. These blocks are therefore identified as "prime (')) numbers." For example, in FIG. 11A, input block 232 is identified as holding or having input therein x and y coordinates obtained from the rare cell (FAST) scanner for the, (i) origin reticle, (ii) y-reticle, (iii) x-reticle, and (iv) size of the sample. Block 232' of FIG. 12 holds similar information, but from the microscope coordinate system. This information is used by the described relationships described in parameter blocks 234 and 236 of FIG. 11A. It is to be noted since the same relationships are used, blocks 234 and 236 are numbered the same in FIG. 12. The input block 238' of FIG. 12, includes the same input areas as 238 of FIG. 11A, but is for data related to the scanner image coordinate system. This information is used in parameter blocks 240, 242 and 244, which contain the same relationships as described in connection with FIGS. 11A-11D.

Similarly, blocks 246', 248' and 250' of FIG. 12 are microscope coordinate system columns which correlate to scanner columns 246, 248 and 250 of FIGS. 11A-11D. It is to be noted that in columns 248 and 250, the relationships are the same as that set forth in the discussion of FIGS. 11A-11D, but the values input would be the Microscope HIT Data values of column 246'.

Independent coordinates column 252' of FIG. 12, also corresponds to independent coordinate column 252 of FIG. 11A-11D. Again, the distinction is that the values being provided are from the microscope coordinate system. As with the discussion related to the preceding columns, similar observations are made with respect to the Skewed and Scaled image coordinates column 254', and the Rotated image coordinates column 256'. Lastly, column 258' displays the converted image coordinates in the scanner coordinate space.

This modularized system therefore permits a user to transfer between the two coordinate spaces, rather than only permitting transformations in a single direction.

The system 230 of FIGS. 11A-11D and 12 is designed for substantially automated operation. The user simply needs to input coordinate information into blocks 232 and 238, and thereafter enter the position information for an object of interest in columns 260 and 262. Thereafter, the system automatically provides the converted microscope coordinate data.

It is to be appreciated, the described system may be designed where the entry of the information is fully automated. Particularly, inputting of the sample into the imaging system allows, the imaging system to obtain information regarding coordinate positions for block 232, and automatically insert this information into the software program. Thereafter, through normal conveyor operations such as depicted, for example, in FIG. 4A-4C, the sample may be automatically moved into a higher resolution device such as the microscope system, where the position in the microscope environment is automatically determined and also entered into blocks 238. Thereafter the position date of objects of interest are provided automatically to block 260, 262.

Figure 13:
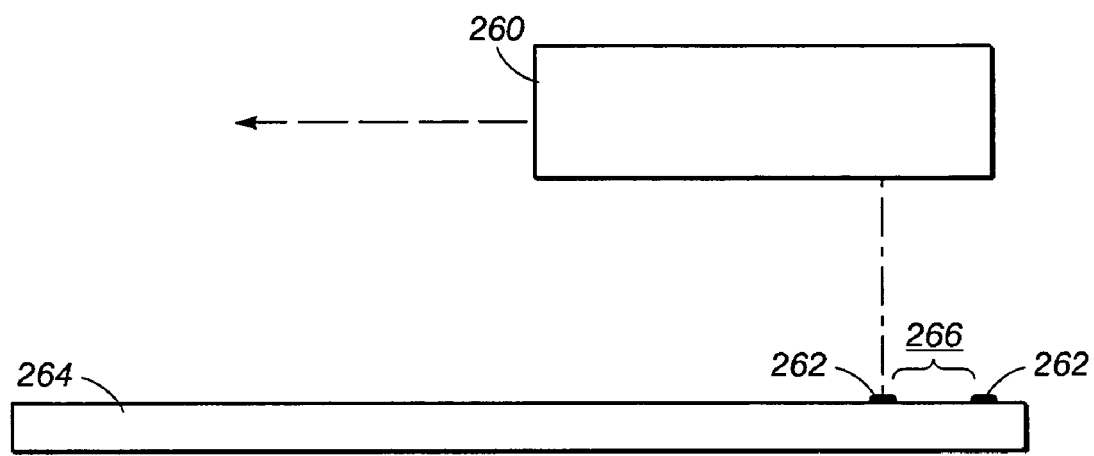
FIG. 13 depicts an embodiment where a marking system directly applies marking material to a slide to identify objects of interest.

Still further, returning to the embodiment related to FIGS. 8 and 9, it is noted circular images 202 are shown on an electronic screen image. It is to be appreciated this embodiment is also meant to represent a physical marking on the sample itself. Particularly, as shown in FIG. 13, automated marking system 260 is moved and positioned to provide marks 262 (whether circular or other form) directly onto slide 264. The marks are placed in association with objects 266 of interest. Using this system, a permanent record of the position of the objects of interest are obtained. The locations for printing are determined in the printing device by a same process as described for determining locations of objects by the microscope system. The marking system may be any known marking system capable of printing in small enough amounts, onto appropriate substrates, such as glass.

Examples of appropriate marking systems may be piezoelectric, acoustic or laser printers, among others. An advantage of using this printing operation is that the samples do not need to be accompanied by a data file of object locations subsequent to the printing. This may be an implementation which finds its usefulness in non-automated clinical settings.

Another aspect of the present embodiments is to include any known (fixed) non-linear imperfections in the scanner into the conversion process (i.e., scan non-linearity). Real-time non-linear imperfections may also be addressed in the conversion process by having the described position measuring system perform real-time position measuring.

The application has been described with reference to the preferred embodiments. Obviously, modifications and alterations will occur to others upon reading and understanding the preceding detailed description. It is intended that the invention be construed as including all such modifications and alterations insofar as they come within the scope of the appended claims or the equivalents thereof.

The invention claimed is:

1. A method for obtaining a position of an object comprising:
    positioning a slide carrying at least one object and having reticle marks arranged at positions which form substantially a right angle, in a slide holder of a first imaging system;
    defining a first coordinate space of the first imaging system;
    designating coordinates of the reticle marks in the first coordinate space;
    defining a second coordinate space of a second imaging system;
    designating the coordinates of the reticle marks in the second coordinate space;
    computing coordinate conversion parameters using the designated coordinates of the reticle marks of the first coordinate space;
    designating coordinates of the at least one object in the first coordinate space; and
    converting the first coordinate space coordinates of the at least one object into unique coordinates in the second coordinate space, using the coordinate conversion parameters.

2. The method according to claim 1, wherein the converting is a linear process.

3. The method according to claim 2, wherein the converting includes a rotation operation.

4. The method according to claim 2, wherein the coordinate conversion includes a scaling operation.

5. The method according to claim 2, wherein the coordinate conversion includes a shifting operation.

6. The method according to claim 2, wherein the coordinate conversion includes a skewing operation.

7. The method according to claim 1, wherein the converting includes converting known non-linear imperfections in one of the first or second coordinate spaces.

8. The method according to claim 1, wherein the converting includes recorded non-linear imperfections in either the first or second coordinate spaces obtained during the process of defining the coordinate space.

9. The method according to claim 1, wherein the unique coordinates in the second coordinate space are used to control movement of an x-y stage.

10. The method according to claim 1, wherein the unique coordinates in the second coordinate space are used to position an identifying mark on the object holder to visually identify the object.

11. The method according to claim 1, wherein the converting further proceeds from the second coordinate space to the first coordinate space.

12. A planar object position locator comprising:
    a first imaging system having a first coordinate space, wherein image location data of an image sample are defined as first coordinates of the first coordinate space;
    a second coordinate space, wherein image location data of the imaged sample are defined as second coordinates of the second coordinate space;
    and a coordinate position conversion system configured to receive the first coordinate location data and generate second imaging system having a second coordinate location data corresponding to the first coordinate location data.

13. The locator according to claim 12, wherein one of the first or second imaging systems is a fast scanner scan system.

14. The locator according to claim 13, wherein the fast scanner system includes,
    a translation stage that supports the sample having a biological smear;
    a fiber optic bundle having a proximate bundle end of first fiber ends arranged to define an input aperture viewing the biological smear on the translation stage, and a distal bundle end of second fiber ends arranged to define an output aperture shaped differently from the input aperture and disposed away from the translation stage;
    a scanning radiation source arranged in fixed relative position to the input aperture, the scanning radiation source scanning a radiation beam on the biological smear within a viewing area of the input aperture, the radiation beam interacting with the biological smear to produce a light signal that is received by the input aperture and transmitted via the fiber optic bundle to the output aperture;
    a photodetector arranged to detect the light signal at the distal bundle end; and
    a processor that processes the light signal detected by the photodetector to identify existence of rare cells in the biological smear.

15. The locator according to claim 12, wherein at least one of the first imaging system and the second imaging system is a fluorescent microscope.

16. The locator according to claim 12, wherein the coordinate position conversion system is further configured to receive the second coordinate location data and generate the first coordinate location data.

17. A method of determining location position data of a planar object comprising:
    designating first coordinate space coordinates of a sample within a first coordinate space;
    designating coordinates of the sample within a second coordinate space;
    applying the second coordinate space coordinates to second conversion parameters;
    selecting first coordinate space object coordinates of an object of the sample, wherein the selected first coordinate space object coordinates are within the first coordinate space;
    applying the selected first coordinate space object coordinates to the first conversion parameters;
    converting the selected first coordinate space object coordinates of the first coordinate space to independent space object coordinates of an independent coordinate space, by the application of the first conversion parameters;

applying the independent space object coordinates to the second conversion parameters; and converting the independent space object coordinates of the independent coordinate space to second coordinate space object coordinates, by the application of the second conversion parameters.

18. The method according to claim 17, wherein the converting includes a rotation operation.

19. The method according to claim 17, wherein the coordinate conversion includes a scaling operation.

20. The method according to claim 17, wherein the coordinate conversion includes a shifting operation.

21. The method according to claim 17, wherein, the coordinate conversion includes a skewing operation.

22. The method according to claim 17, wherein the coordinates in the second coordinate space are used to control movement of an x-y stage.

23. The method according to claim 17, wherein the coordinates in the second coordinate space are used to position an identifying mark on the object holder to visually identify the object.

* * * * *